(12) United States Patent
Hladio et al.

(10) Patent No.: US 9,987,092 B2
(45) Date of Patent: Jun. 5, 2018

(54) COMPUTER-ASSISTED JOINT REPLACEMENT SURGERY AND PATIENT-SPECIFIC JIG SYSTEMS

(71) Applicant: Intellijoint Surgical Inc., Waterloo (CA)

(72) Inventors: Andre Novomir Hladio, Ottawa (CA); Richard Tyler Fanson, Kitchener (CA); Armen Garo Bakirtzian, Kitchener (CA)

(73) Assignee: INTELLIJOINT SURGICAL INC., Waterloo (CA)

( * ) Notice: Subject to any disclaimer, the term of this patent is extended or adjusted under 35 U.S.C. 154(b) by 525 days.

(21) Appl. No.: 14/409,819

(22) PCT Filed: Jun. 20, 2013

(86) PCT No.: PCT/CA2013/000587
§ 371 (c)(1),
(2) Date: Dec. 19, 2014

(87) PCT Pub. No.: WO2013/188960
PCT Pub. Date: Dec. 27, 2013

(65) Prior Publication Data
US 2015/0182292 A1    Jul. 2, 2015

Related U.S. Application Data

(60) Provisional application No. 61/662,018, filed on Jun. 20, 2012.

(51) Int. Cl.
*A61B 17/56* (2006.01)
*A61B 17/17* (2006.01)
(Continued)

(52) U.S. Cl.
CPC ............ *A61B 19/46* (2013.01); *A61B 5/1114* (2013.01); *A61B 5/4836* (2013.01);
(Continued)

(58) Field of Classification Search
CPC ................ A61B 19/46; A61B 19/5525; A61B 34/00–2034/258; A61B 17/1742
See application file for complete search history.

(56) References Cited

U.S. PATENT DOCUMENTS

| | | |
|---|---|---|
| 6,241,735 B1 | 6/2001 | Marmulla |
| 6,738,657 B1 | 5/2004 | Franklin et al. |

(Continued)

FOREIGN PATENT DOCUMENTS

| | | | | |
|---|---|---|---|---|
| GB | 2382777 A | 6/2003 | | |
| WO | WO 2010063117 A1 * | 6/2010 | ........... | A61F 2/4609 |
| WO | 2010124164 A1 | 10/2010 | | |

OTHER PUBLICATIONS

International Search Report dated Sep. 6, 2013, issued by the Canadian Intellectual Property Office for International PCT Patent Application No. PCT/CA2013/000587.

(Continued)

*Primary Examiner* — Zade Coley

(57) ABSTRACT

Provided are methods and systems related to computer-assisted joint replacement surgery, and corresponding instrumentation systems. In one example, there is provided a system for guided surgery comprising: a sensor for coupling to a first bone to receive positional signals; a beacon for coupling to an object to provide the positional signals to the sensor, the object comprising one of a second bone and a surgical tool; a patient-specific jig (PSJ) for guiding a relative position of the sensor and the first bone during coupling to position the sensor in a predetermined pose in an anatomical coordinate frame; and an intra-operative computing unit in communication with the sensor, the intra-operative computing unit configured to calculate poses of the beacon with respect to the anatomical coordinate frame utilizing pre-operative data representing the PSJ and display positional information for the object in real time.

21 Claims, 13 Drawing Sheets

(51) Int. Cl.
*A61B 19/00* (2006.01)
*A61B 5/11* (2006.01)
*A61B 90/96* (2016.01)
*A61B 90/00* (2016.01)
*A61B 5/00* (2006.01)
*A61B 34/20* (2016.01)
*A61B 34/00* (2016.01)
*A61B 34/10* (2016.01)

(52) U.S. Cl.
CPC ........ *A61B 17/175* (2013.01); *A61B 17/1742* (2013.01); *A61B 17/1746* (2013.01); *A61B 34/20* (2016.02); *A61B 90/06* (2016.02); *A61B 90/37* (2016.02); *A61B 90/96* (2016.02); *A61B 5/6878* (2013.01); *A61B 34/25* (2016.02); *A61B 2017/568* (2013.01); *A61B 2034/108* (2016.02); *A61B 2034/2055* (2016.02)

(56) References Cited

U.S. PATENT DOCUMENTS

| | | | |
|---|---|---|---|
| 7,618,451 B2* | 11/2009 | Berez | A61B 5/1076 606/84 |
| 7,634,119 B2 | 12/2009 | Tsougarakis et al. | |
| 7,634,306 B2* | 12/2009 | Sarin | A61B 5/103 600/426 |
| 8,083,745 B2 | 12/2011 | Lang et al. | |
| 8,133,234 B2 | 3/2012 | Meridew et al. | |
| 8,160,345 B2 | 4/2012 | Pavlovskaia et al. | |
| 8,167,823 B2 | 5/2012 | Nycz et al. | |
| 8,175,683 B2 | 5/2012 | Roose | |
| 9,775,625 B2 | 10/2017 | Schoenefeld | |
| 2009/0222016 A1* | 9/2009 | Park | A61B 17/175 606/89 |
| 2011/0160583 A1 | 6/2011 | Roche et al. | |
| 2011/0160736 A1* | 6/2011 | Meridew | A61B 17/15 606/89 |
| 2011/0184419 A1* | 7/2011 | Meridew | A61B 17/151 606/80 |
| 2011/0190775 A1 | 8/2011 | Ure | |
| 2011/0218545 A1* | 9/2011 | Catanzarite | A61B 17/155 606/96 |
| 2011/0224674 A1* | 9/2011 | White | A61B 17/1617 606/91 |
| 2012/0157887 A1 | 6/2012 | Fanson et al. | |

OTHER PUBLICATIONS

Extended European Search Report dated Jan. 22, 2016 Issued by the European Patent Office for Corresponding European Patent Application No. 13806755.8.

* cited by examiner

COMPUTER-ASSISTED JOINT REPLACEMENT SURGERY AND PATIENT-SPECIFIC JIG SYSTEMS

FIELD

The present disclosure relates generally to systems and method for guided surgery including computer-assisted joint replacement surgery and patient-specific jig systems.

BACKGROUND

In many surgical procedures, including joint replacement such as Total Hip Arthroplasty (THA), achieving precise positioning of tools and implants with respect to a patient's anatomy is critical for successful outcomes. Positioning prosthetic implants relative to the patient's anatomy may involve numerous challenges such as, selecting the correct implant geometry and altering the patient's bony anatomy (e.g. reaming, osteotomy, etc.), among others. Some important goals for a successful THA, for example, include: proper alignment of the acetabular cup; restoration or correction of leg length and offset; restoration of hip center-of-rotation (COR); and stability of new hip joint. The surgeon is often required to make various accurate assessments intra-operatively. Pre-operative planning may assist with the surgery and patient-specific jigs for guiding particular procedures may be formed using data gathered during a pre-operative phase. Intra-operatively, a guidance system may also be used, for example, for tracking relative positions of objects such as bones and/or tools during surgery.

SUMMARY

The methods and systems described herein relate to computer-assisted joint replacement surgery, and corresponding instrumentation systems. In one example, there is provided a system for guided surgery comprising: a sensor for coupling to a first bone to receive positional signals; a beacon for coupling to an object to provide the positional signals to the sensor, the object comprising one of a second bone and a surgical tool; a patient-specific jig (PSJ) for guiding a relative position of the sensor and the first bone during coupling to position the sensor in a predetermined pose in an anatomical coordinate frame; and an intra-operative computing unit in communication with the sensor, the intra-operative computing unit configured to calculate poses of the beacon with respect to the anatomical coordinate frame utilizing pre-operative data representing the PSJ and display positional information for the object in real time. The PSJ may be configured to guide an insertion of at least two bone pins into the first bone and the sensor is configured to be rigidly attached to the at least two bone pins.

In another example there is further provided a system for guided surgery comprising: a sensor for coupling to a first bone to receive positional signals; a patient specific jig (PSJ) configured to mate with the first bone and mount a beacon via the PSJ to the first bone; a first beacon to provide the positional signals to the sensor, the first beacon for mounting to the first bone by the PSJ; a second beacon to provide the positional signals to the sensor, the second beacon for coupling to an object comprising one of a second bone and a surgical tool; an intra-operative computing unit in communication with sensor, the intra-operative computing unit configured to: measure a pose of the first beacon when coupled to the bone via the PSJ to establish a positional relationship between the sensor and the PSJ; calculate poses of the second beacon with respect to an anatomical coordinate frame utilizing pre-operative data representing the PSJ and the positional relationship between the sensor and the PSJ; and display positional information for the object in real time. The first beacon and PSJ may be integrally formed. The first beacon and second beacon may be a single beacon, the first beacon being removable from the PSJ for coupling to the object.

In these system examples, the surgery may be a Total Hip Arthroplasty. The PSJ may be a patient-specific acetabular jig. The object may be the second bone and the system may further comprise a second PSJ for coupling a beacon to the second bone. The pre-operative data may be encoded on one of the PSJ and the beacon and the sensor may be configured to communicate the pre-operative data to the computing unit.

In one example, there is provided a computer implemented method for tracking intra-operatively an object using a sensor to receive positional signals from a beacon, the sensor coupled to a first bone in a predetermined pose in an anatomical coordinate frame via a patient-specific jig (PSJ), the beacon coupled to the object, which object comprises one of a second bone and a surgical tool, the method comprising: receiving positional information from the sensor at an intra-operative computing unit in communication with the sensor; calculating poses of the beacon with respect to the anatomical coordinate frame utilizing pre-operative data representing the PSJ; and displaying positional information for the object in real time. The first bone may be an acetabulum and the PSJ may be pre-operatively formed to mate with the acetabulum. The object may be a femur and a second PSJ may couple the beacon to the femur and a calculating step may further utilize pre-operative data representing the second PSJ.

In another example, there is provided computer implemented method for tracking intra-operatively an object using a sensor to receive positional signals from a first beacon and a second beacon, the sensor coupled to a first bone, the first beacon coupled to the first bone via a patient specific jig (PSJ) configured to mate with the first bone, the second beacon coupled to the object, which object comprises one of a second bone and a surgical tool, the method comprising: receiving positional information from the sensor at an intra-operative computing unit in communication with the sensor; measuring a pose of the first beacon when coupled to the first bone via the PSJ to establish a positional relationship between the sensor and the PSJ; calculating poses of the second beacon with respect to an anatomical coordinate frame utilizing pre-operative data representing the PSJ and the positional relationship between the sensor and the PSJ; and displaying positional information for the object in real time. The first bone may be an acetabulum and the PSJ may be pre-operatively formed to mate with the acetabulum. The object may be a femur and a second PSJ may couple the second beacon to the femur and a calculating step may further utilize pre-operative data representing the second PSJ.

In these method examples, the PSJ may be pre-operatively formed based on an output of pre-operative planning software. Initial positional data may be measured using the pre-operative planning software and the method may comprise comparing the poses calculated with the initial positional data and presenting results of the comparing. The initial positional data may include one or more of: leg length, offset and hip center of rotation.

There is provided a system for verifying a patient-specific jig (PSJ) configured for a specific patient comprising: an optically readable verification feature pre-operatively associated with the PSJ; a sensor to read the optically readable verification feature and communicate verification feature information, the sensor further configured to track a pose of a beacon during surgery; and an intra-operative computing unit for communication with the sensor, the intra-operative computing unit configured to cross-check the verification feature information received with pre-operative verification information associated with the PSJ and the specific patient. The verification feature may be a barcode. The verification feature may be a positional configuration of markers of the beacon provided for the PSJ. The verification feature may be on the PSJ. The verification feature may be on the beacon provided for coupling with the PSJ. The verification feature may encode data output from software for pre-operative planning for making the patient specific jig.

There is provided a patient-specific jig for facilitating a guided surgical procedure comprising: a mirroring surface pre-operatively formed to mirror a surface of a bone of a patient; a mechanical connection point for removably coupling one of a beacon and a sensor; and a second surface to guide a cut of the bone. The bone may be a femur. The second surface may guide a resection of a femoral head of the femur. The bone may be a tibia. The guided surgical procedure may be a Total Hip Arthroplasty. The patient-specific jig may comprising one or more additional surfaces to guide additional cuts.

Other aspects described herein will be apparent to those of ordinary skill in the art.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the claimed systems and methods.

INCORPORATION BY REFERENCE

Figure 1:
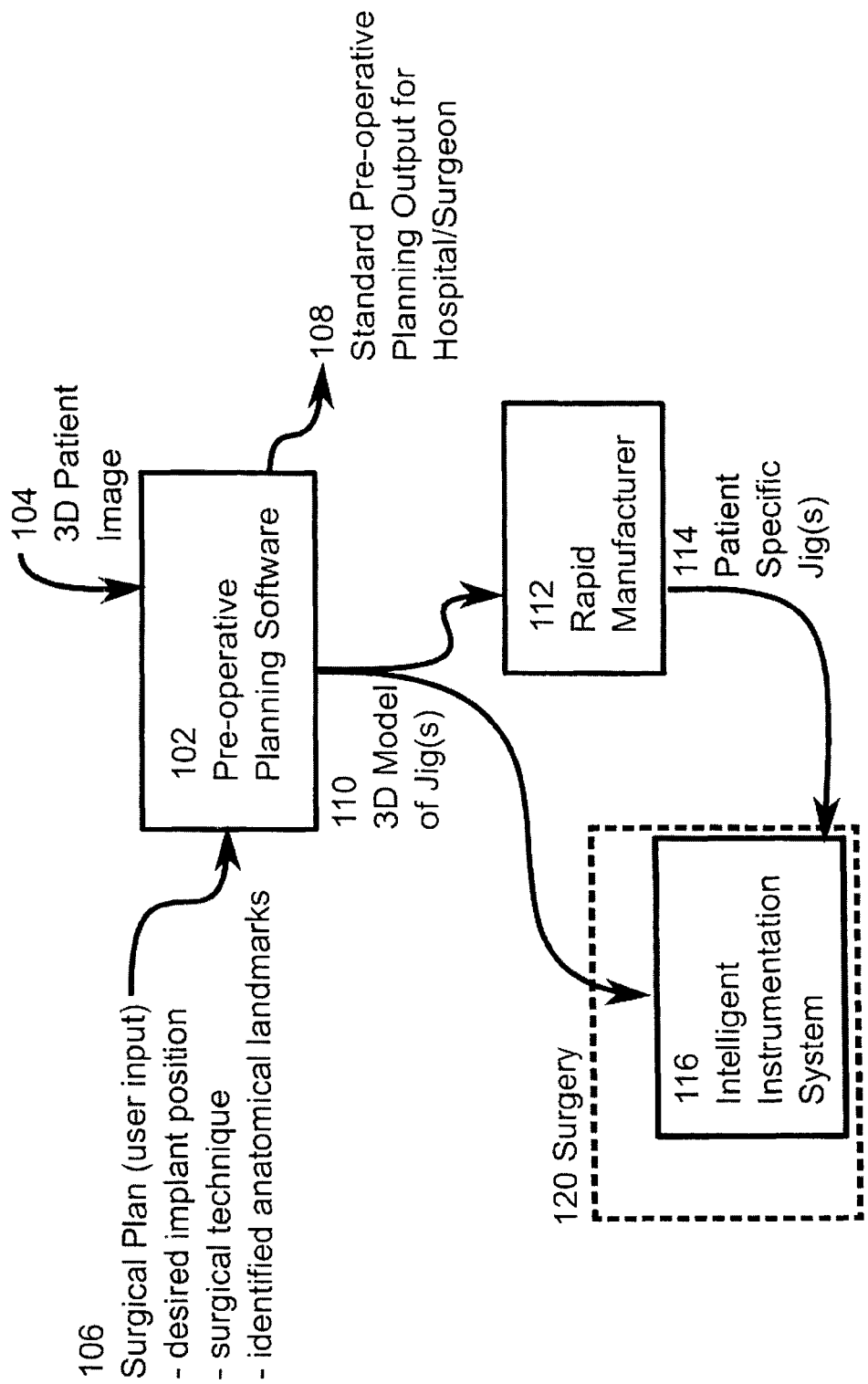
FIG. 1 is a block diagram illustrating the input-output interconnections between various aspects related to one example presented.

Except for any term definitions that conflict with the term definitions provided herein, the following related, co-owned, and co-pending U.S. patent application Ser. No. 13/132,115 filed Dec. 2, 2009 entitled "Method and system for aligning a prosthesis during surgery using active sensors"; 61/424,447, filed Dec. 17, 2010 and entitled "Method And System For Aligning A Prosthesis During Surgery"; Ser. No. 13/328,997, filed Dec. 16, 2011 and entitled "Method And System For Aligning A Prosthesis During Surgery"; Ser. No. 13/445,777 filed Apr. 12, 2012 and entitled "Computer-Assisted Joint Replacement Surgery And Navigation Systems"; and 61/662,018 filed Jun. 20, 2012 and entitled "Computer-Assisted Joint Replacement Surgery And Patient-Specific Jig Systems" are incorporated herein by reference, in their entirety.

Additionally, except for any term definitions that conflict with the term definitions provided herein, the following U.S. Patents and Published Application Nos. are incorporated herein by reference, in their entirety: U.S. Pat. No. 8,175,683 issued May 8, 2012 and entitled "System And Method Of Designing And Manufacturing Customized Instrumentation For Accurate Implantation Of Prosthesis By Utilizing Computed Tomography Data; U.S. Pat. No. 8,167,823, issued May 1, 2012 and entitled "Method And Apparatus For Aligning And Securing An Implant Relative To A Patient"; U.S. Pat. No. 8,160,345, issued Apr. 17, 2012 and entitled "System And Method For Image Segmentation In Generating Computer Models Of A Joint To Undergo Arthroplasty"; U.S. Pat. No. 8,133,234, issued Mar. 13, 2012 and entitled "Patient Specific Acetabular Guide And Method"; U.S. Pat. No. 8,083,745, issued Dec. 27, 2011 and entitled "Surgical Tools For Arthroplasty"; U.S. Pat. No. 7,634,119, issued Dec. 15, 2009 and entitled "Fusion Of Multiple Imaging Planes For Isotropic Imaging In MRI And Quantitative Image Analysis Using Isotropic Or Near-Isotropic Imaging; U.S. Pat. No. 7,618,451, issued Nov. 17, 2009 and entitled "Patient Selectable Joint Arthroplasty Devices And Surgical Tools Facilitating Increased Accuracy, Speed And Simplicity In Performing Total And Partial Joint Arthroplasty"; US Pub. No. 2011/0224674, published Sep. 15, 2011 and entitled "Patient-Specific Acetabular Alignment Guides"; US Pub. No. 2011/0190775, published Aug. 4, 2011 and entitled "Device And Method For Achieving Accurate Positioning Of Acetabular Cup During Total Hip Replacement; US Pub. No. 2011/0184419, published Jul. 28, 2011 and entitled "Patient-Specific Acetabular Guides And Associated Instruments; US Pub. No. 2011/0160583, published—Jun. 30, 2011—and entitled "Orthopedic Navigation System with Sensorized Devices; and US Pub. No. 2009/0222016, published Sep. 3, 2009 and entitled "Total Hip Replacement Surgical Guide Tool".

DEFINITIONS

Prior to describing the present methods and systems in detail, it is useful to provide definitions for key terms and concepts used herein. Unless defined otherwise, all technical and scientific terms used herein have the same meaning as commonly understood by one of ordinary skill in the art to which these methods and systems belong.

"Patient-specific": The term patient-specific generally refers to the customized creation of a surgical instrument, component, or jig, for the particular patient that is undergoing the surgery. In one example, a patient-specific jig is an orthopedic jig formed by rapid-manufacturing techniques (e.g., three-dimensional (3D) printing, CNC machining), based on a 3D image reconstruction of one or more surfaces of the patient's bony anatomy. Other examples include instruments, components, and/or jigs formed, molded, or otherwise created to mate with one or more corresponding surfaces of the patient's anatomy. Additional examples of systems and methods for creating and/or imaging patient-specific orthopedic jigs and/or anatomical surfaces are discussed in the above incorporated patents and published applications; e.g., U.S. Pat. Nos. 8,160,345; 8,083,745; 7,634,119; 7,618,451; and 2011/0190775.

"Positional Relationship" or "Relative Position" or "pose": The terms "positional relationship" or "relative position" or "pose" generally refer to a rigid-body transformation between coordinate systems. In Cartesian space, the rigid-body transformation consists of six degrees-of-freedom (DOF): 3-DOF for translational position and 3-DOF for rotational (or orientation) position. In general, the terms "positional relationship" or "relative position" or "pose" encompass one through six DOF. The number of DOF of a positional relationship may be explicitly stated (e.g., 2-DOF), or implied by the context (e.g., 3-DOF are generally used to describe orientation). For example, in some instances, positional relationship is determined by first determining the 6-DOF positioning, then extracting the desired positional information described by less than 6-DOF.

Intelligent Instrumentation: As used herein, intelligent instrumentation refers to combining sensor units with surgical instrumentation, such that the relative position and/or orientation of surgical instruments and/or implants with respect to a patient's anatomy may be calculated and displayed in real-time intra-operatively (e.g. guided surgery). This may be accomplished by a first sensor unit providing positional signals, and a second sensor unit receiving positional signals. An example of an intelligent instrumentation system based on optical sensor units is presented in co-pending U.S. patent application Ser. No. 13/328,997, which has been incorporated by reference herein.

Before the present methods and systems are described in greater detail, it is to be understood that they are not limited to particular examples described, and as such may vary. It is also to be understood that the terminology used herein is for the purpose of describing particular examples only, and is not intended to be limiting. The scope of the present systems and methods will be limited only by the appended claims.

DETAILED DESCRIPTION

Presented herein are systems and methods to aid a surgeon in understanding pre- and post-operative parameters of interest in positionally guided surgery. For example, the systems and methods presented herein monitor operative parameters of interest by combining intelligent instrumentation (i.e. sensorized surgical instruments) with patient-specific jigs, used to map a patient's bony anatomy. Operative parameters of interest are then measured, determined, and conveyed to a surgeon, intra-operatively, in a meaningful way. Intelligent instrumentation in combination with patient-specific orthopedic jigs (i.e., jigs formed specifically for the patient), provides several unique clinical advantages.

In general, joint replacement surgery involves replacing an existing joint with artificial prosthetic components. Examples of common joint replacements include hip replacements and knee replacements. For ease of explanation, the systems and methods described herein are described with reference to performing a Total Hip Arthroplasty (THA) procedure. However, it will be evident to a person of skill in the art that the systems and methods presented may be applied to other types of hip replacement (e.g., hip resurfacing, revision hip replacement, etc.), as well as to other surgical procedures (e.g., joint replacement surgery for the knee, shoulder, ankle, pedicle screw placement, osteotomies, navigated biopsies etc.).

Total Hip Arthroplasty (THA), also called primary hip replacement, involves the surgical excision of the head and proximal neck of the femur, and the removal of the acetabular cartilage and subchondral bone. An artificial canal is created in the proximal medullary region of the femur, and a metal femoral prosthesis is inserted into the femoral medullary canal. An acetabular component (or implant) is then inserted in the enlarged acetabular space, and a reduction procedure is then performed to mate the femoral prosthesis with the acetabular component. More detailed descriptions of THA are provided in the above-referenced patents and patent applications; e.g., U.S. patent application Ser. Nos. 13/328,997 and 13/445,777.

An important aspect of THA (or any joint replacement surgery) is identifying the relative position between anatomical structures and/or the prosthesis before and after the dislocation, implantation, and reduction procedures. Accurate placement of an implant relative to the patient's anatomy requires highly-trained surgeons to make real-time intra-operative decisions. Mechanical guides have been developed to aid surgeons during intra-operative procedures. Mechanical guides, however, tend to be cumbersome and lack the flexibility of allowing a surgeon to make intra-operative adjustments to a pre-operative plan. Computer-assisted navigation systems are also available. Traditional computer-assisted navigation systems use expensive optical equipment to "follow" optical markers on tagged anatomical structures during intra-operative procedures. Such systems require: 1) registrations of multiple anatomical structures (e.g., pelvic registration and femoral registration); 2) markers positioned on respective anatomical structures; and 3) fixed stereoscopic camera units stationed within the operating room to monitor the movements of the markers throughout the surgery. Such systems also suffer from line-of-site limitations, are cumbersome, and lack the flexibility to perform intra-operative adjustments to a pre-operative plan.

Another important aspect of THA is ensuring proper alignment of the acetabular component (or implant) with respect to the pelvis. The orientation of an acetabular component with respect to the pelvis anatomy is defined by angles of abduction and anteversion.

Still another important aspect of hip replacement is ensuring an acceptable post-reduction leg length and offset. Typically, the goal is to leave the leg length and offset unchanged as a result of the THA. However, surgeons will often incorporate a small change in leg length as a corrective measure. Therefore, surgeons benefit from a precise understanding of pre-dislocation and post-reduction leg length and offset changes (as well as changes in anterior-posterior (AP) position and center of rotation (COR) of the femur). The original leg length and offset and COR location may be measured using a pre-operative scan (e.g., X-ray, CT scan, and MRI). A desired change in leg length and offset may be calculated based on a desired resulting leg length and offset, the original leg length and offset, the resulting COR, as well as the geometrical dimensions of the femoral implant.

As known to those skilled in the art, anatomical registration (pelvic and/or femoral) is one of the biggest barriers to adoption of navigation systems for hip arthroplasty. Registration is often time consuming, and potentially inaccurate. The systems and methods presented herein, however, employ patient-specific jigs, formed based on pre-operative 3D image reconstruction of the patient's anatomical structures, with relative positioning determinable by the pre-operative formation of the jig, which obviates the difficulties with traditional registration. As a result, measurements which the system provides to the surgeon may be more accurate; particularly because the sensor/patient interface (via the patient-specific jig) matches the anatomy of the patient.

With application to THA, the systems and methods presented herein may be used to intra-operatively measure/assess: leg length, offset, and/or anterior-posterior position change; change in hip center of rotation location; acetabular cup positioning (e.g., angles of abduction and/or anteversion); reaming depth and alignment of an acetabular reamer; femoral version; and combined anteversion (e.g., combination of femoral version and cup anteversion).

While various examples are presented herein, the systems and methods generally include one or more of the following three components: 1) intelligent instrumentation, capable of position and/or orientation measurements; 2) one or more patient specific jigs; and 3) pre-operative planning software, executing on a pre-operative computing unit (e.g. personal computer, laptop, tablet, smartphone, network computer, etc).

In general, intelligent instrumentation includes one or more of the following three sub-systems: 1) at least two sensor units (e.g. one is configured to receive or read positional signals and another configured to provide or emit positional signals) capable of relative pose measurement, for operative coupling to surgical instruments, bones, implants, mechanical interfaces and/or bone fixation tools, 2) an intra-operative computing unit capable of communication with one or more sensor units and providing a display (e.g. a personal computer, laptop, tablet, smartphone, embedded system, etc), and 3) intra-operative software running on the intra-operative computing unit, which performs various calculations and displays important parameters to surgeons. To preserve clarity, the systems and methods described herein will be described using an instance of intelligent instrumentation, comprising an optical sensor (for coupling to a bone) to receive positional signals, an optically trackable beacon to provide positional signals, and an intra-operative computing unit, which executes software. Other sensing modalities, and/or other configurations will be evident to those skilled in the art as qualifying as intelligent instrumentation.

In general, the primary function of a patient specific jig (PSJ), in the context of this system and method, is to facilitate a coordinate mapping from the intelligent instrumentation (e.g. an optical sensor) to an anatomical coordinate frame (i.e. a patient's bony anatomy), such that position and/or orientation measurements may be calculated relative to the patient's anatomy, rather than in an arbitrary coordinate frame. As such, a PSJ may have a surface which mirrors the surface of a patient's bone, such that the PSJ may mate with the corresponding bone in a unique pose, when the mirroring surfaces contact each other. With application to THA, it will be clear that a PSJ may have secondary functions as well.

With application to THA, a system includes intelligent instrumentation, in combination with pre-operative planning software, configured to utilize a patient specific acetabular jig and/or a patient specific femoral jig.

The patient specific acetabular jig (or PSA) is generally used to either: install a pelvis sensor (e.g., optical reader) in a known positional relationship with respect to the pelvis (i.e., the sensor is "inherently registered" to the anatomical coordinate frame); or identify a positional relationship between the pelvis sensor and the pelvis via an additional beacon coupled to the PSA (effect registration via single measurement). The PSA can also be used to determine the location of the pre-operative COR, as well as determine a pre-operative baseline leg length and offset, of the hip joint with respect to the pelvis sensor during surgery.

The patient specific femoral jig (PSF) is used to provide a "low profile" attachment point for a femur sensor unit (e.g., optical beacon). The PSF is also used to provide a mechanical guide to assist the surgeon with resecting the femoral head according to a pre-operative plan. The PSF may also provide a known positional relationship between the attachment point (and hence femur sensor unit) and certain anatomical femoral features; including: direction of leg length; direction of offset; principle anatomical planes (coronal, sagittal, transverse); the line representing the intersection of the coronal and transverse planes is particularly important in defining femoral version; pre-operative femoral version; and/or reference points with respect to pelvis (for initial leg length/offset baseline).

The pre-operative planning (POP) software, into which imaging (e.g. MRI, CT, etc.) of the patient's anatomy is inputted, is used to create a procedure plan, particularly considering implant sizing, selection, and positioning. The data output of the POP software is used to rapidly manufacture patient-specific jigs, as well as is loaded into the intelligent instrumentation system to facilitate real-time guided surgery.

FIGS. 1-14 depict exemplary examples of system components for performing hip replacement surgery in accordance with the systems and methods presented herein.

FIG. 1 illustrates input and output relationships between various aspects and/or steps in the context of systems and methods described herein. Prior to surgery, pre-operative planning is often performed on a pre-operative computing unit, based on imaging (e.g. x-ray, CT, MRI). The pre-operative planning software 102 is used for pre-operative planning, executes on a pre-operative computing unit (e.g. laptop, PC, tablet, etc), and may require the following inputs: a 3D medical image of the surgical site 104 (a digital representation of the patient's anatomy, to facilitate creating a surgical plan), and a surgical plan 106, based on the surgeon's objectives and preferences, as well as the medical image. Examples of a surgeon's objectives and/or preferences may include a desired implant position, desired sizing of implants and/or tools, and the surgical technique of choice (e.g. posterior approach for THA). As part of the surgical plan 106, the surgeon may be required to identify relevant anatomical landmarks on the digital medical image (via the pre-operative software 102) in order to define at least one coordinate frame associated with the anatomy. Alternatively, landmarks may be identified automatically. Typically, the standard output of pre-operative planning 108 includes a pre-operative plan, an estimate of the required resources for surgery. In addition to the standard output 108, output information relating to the 3D model(s) of patient specific jigs 110 is communicated from the POP software 102 to a rapid manufacturer 112, and used to design and fabricate the patient-specific jigs 114. The 3D model output 110 may be communicated to a rapid manufacturer 112 electronically (e.g. via internet, email, secure network, cloud database), or by any other means. The electronic 3D models 110 may be in the form of CAD files, which may be used to fabricate the patient-specific jigs 114 using rapid-prototyping techniques. The POP software 102 may also be used to communicate data to the intelligent instrumentation system 116 (to be loaded into the intra-operative computing unit 216 prior to surgery). The data may include the operative plan, and patient specific jig 114 geometries (based on the 3D jig model(s) 110). Data communication from the pre-operative computing unit to the intelligent instrumentation system 116 may take any form (e.g., CD's, network server, cloud server, USB key, hard drive, paper, bar code labels, etc.). The POP software 102 may also be used to influence hospital purchasing/inventory management (e.g. for orthopedic implants).

Figure 2:
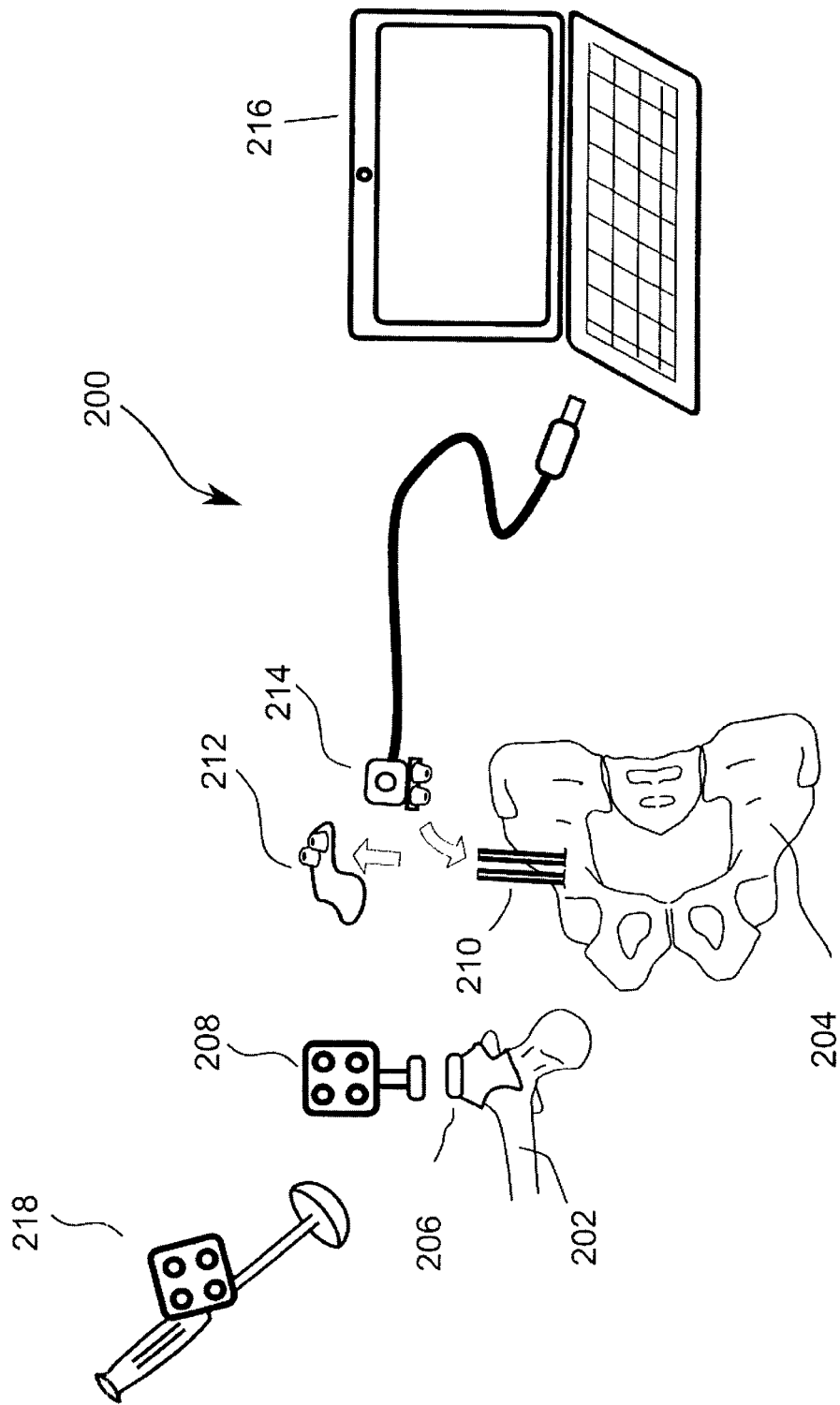
FIG. 2 is an illustration of a surgical guidance system in accordance with one example presented.

FIG. 2 shows an exemplary system 200 with application to THA. A dislocated hip is depicted, comprising a femur 202 and a pelvis 204. A patient specific femur jig 206 is shown mated with a femur 202 in a unique positional relationship. In this case, the PSJ 206 is affixed to the bone during the guided portion of the surgery, and may be coupled in a unique positional relationship with a beacon 208 (the coupling may be a repeatable connection, or the respective components may be integrally formed, during rapid manufacturing 112). On the pelvis 204, a rigid mounting structure 210 is depicted, whose position on the pelvis 204 is controlled by using a PSA jig 212 uniquely mated with the patient's bone during installation (the PSA jig 212 is depicted after removal, by axially sliding off the mounting structure 210, as indicated by an arrow). The mounting structure 210 unique mates with a sensor 214 (depicted as about to be mounted, as indicated by the arrow). The sensor 214 is in communication with an intra-operative computing unit 216, which executes software to process raw data in order to display real-time positional information to a surgeon. A trackable surgical tool 218 (i.e. an instrument with an other optically trackable beacon rigidly affixed in a known pose) is depicted, in this instance as an acetabular cup inserter; however, be evident to those skilled in the art that other surgical instruments may be equivalently used (e.g. reamers, broaches, saws, osteotomes, drills, needles, etc).

Where the PSJ's are used to guide the coupling of the sensor or beacon to a bone, that bone is inherently registered to the sensor or beacon; as such, the software, executing on the intra-operative computing unit 216 does not require functionality or operations for anatomical registration, which may greatly simplify the design and intra-operative use of the software. Alternatively, a sensor or first beacon may be coupled to a bone, and a PSJ, coupled with a second beacon, may be used to determine the positional relationship between the bone and the sensor or first beacon. In this case, the software executing on the intra-operative computing unit 216 would require functionality/algorithms for anatomical registration; however, the anatomical registration of the bone would be based off of a single pose measurement by the intelligent instrumentation.

Figure 3:
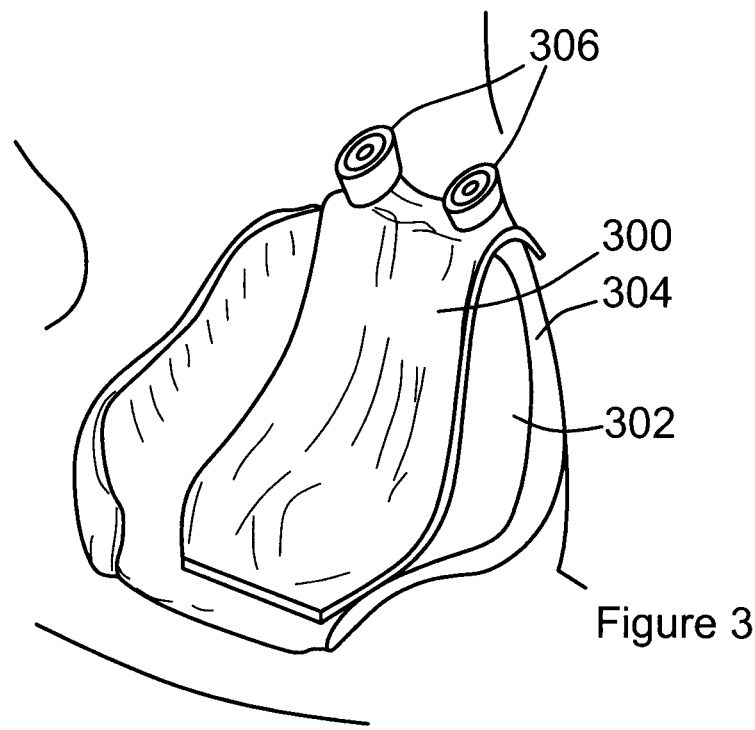
FIG. 3 is an illustration of a patient-specific acetabular jig, in accordance with another example presented.

FIG. 3 is an illustration of a patient-specific acetabular (PSA) jig 300, in accordance with one example presented. The PSA jig 300 is pre-operatively formed so as to include a surface (not shown) that mirrors an anatomical surface of the patient's acetabulum 302. As such, the jig-patient interface provides a determinable relative positioning with respect to any system component that is also coupled to the PSA jig 300. In the example shown in FIG. 3, a pelvis sensor (not shown) can be attached to the pelvis in a unique and pre-determined position via a rigid mounting structure coupled to the pelvis 304 via guides 306 on the PSA jig 300. In practice, screws/pins (e.g. k-wires, Steinmann pins) are inserted through both guides 306. As such, a surface of the PSA jig 300 is being used to guide (or otherwise facilitate) the coupling of the pelvis sensor to the pelvis. The PSA jig 300 can then be removed, leaving the rigid mounting structure (e.g. screws/pins) in place. Because the patient-specific acetabular PSA jig 300 is used to attach the pelvis sensor to the pelvis 304, and because the formation (or specifications, or geometry) of the PSA jig 300 is known, the relative position of the pelvis sensor with the pelvis 304 can be determined.

Figure 4:
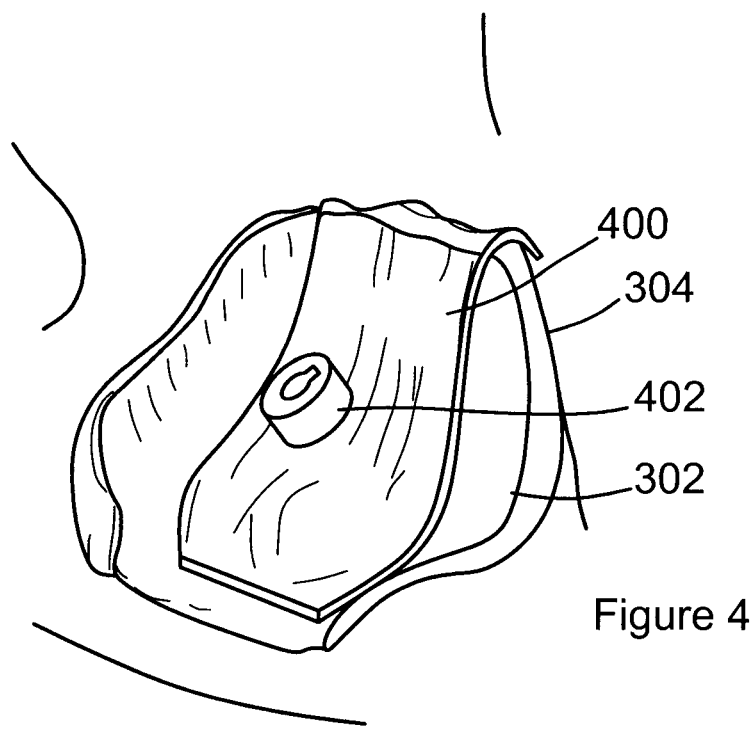
FIG. 4 is an illustration of a patient-specific acetabular jig, in accordance with another example presented.

FIG. 4 is an illustration of an alternative PSA jig 400, in accordance with another example presented. The PSA jig 400 is pre-operatively formed so as to include a surface (not shown) that mates with the anatomical surface of the patient's acetabulum 302. As such, the jig-patient interface provides a determinable relative positioning with respect to any system component that is also coupled to the PSA jig 400. In the example shown in FIG. 4, a pelvis sensor (not shown) can be attached to the pelvis 304 at an arbitrary location (e.g. on the pelvis' iliac crest), and a reference sensor (not shown), which is coupled to a mechanical connector 402, can be used to determine the relative position of the pelvis sensor with respect to the pelvis 304. Because the formation (or specifications) of the PSA jig 400 is known, the relative position of the pelvis sensor can be determined. The PSA jig 400 can then be removed, leaving the pelvis sensor in place. Alternatively, the PSA jig 400 can be coupled to a trackable acetabular instrument (i.e. impactor tool, reamer shaft, etc, coupled with a reference sensor unit for tracking position and/or orientation) via the mechanical connector 402, such that the relative position of the pelvis sensor with respect to the pelvis may be determined.

Figure 5:
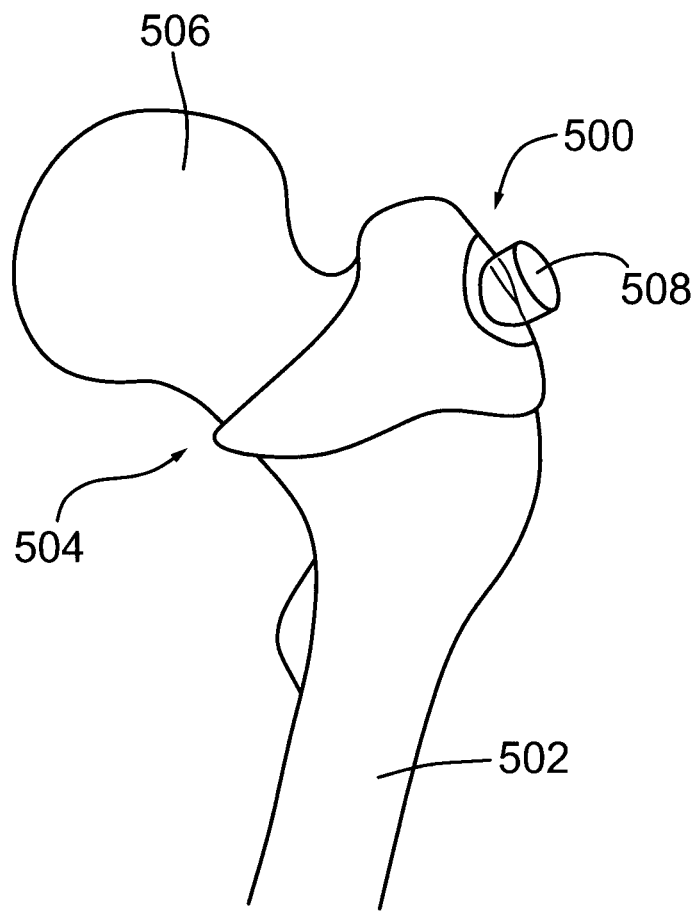
FIG. 5 is an illustration of a patient-specific femoral jig, in accordance with one example presented.

FIG. 5 is an illustration of a patient-specific femoral (PSF) jig 500, in accordance with one example presented. The PSF jig 500) is pre-operatively formed so as to include a surface (not shown) that mirrors an anatomical surface of the patient's femur 502. As such, the jig-patient interface provides a determinable relative positioning with respect to any system component that is also coupled to the PSF jig 500. The PSF jig 500 can serve at least three functions. First, the jig-patient interface of the PSF jig 500 takes the place of typical registration tools, matches the femoral contour, and identifies the femoral anatomy. Second, the PSF jig 500 includes a surface (or platform) 504 to guide a cut (or resection) of the femoral head 506. Third, the PSF jig 500 includes a mechanical connector (or second platform) 508 for attachment (removable, or integral attachment) of a femur sensor unit (not shown). It will be evident to those skilled in the art, that a patient specific jig with these features (namely, mirroring a surface of a bone; providing a mechanical connection for removably coupling a sensor or beacon; and, providing at least one surface to guide a cut of the bone) need not exclusively to proximal femurs in THA, but may be applied to various other bones and/or surgical procedures.

Because of potential difficulties of mating the jig-patient interface of the PSF jig 500 with the femur (e.g., due to muscles and soft tissues between the jig 500 and the femur 502), the jig-patient interface can be formed to mirror the femoral articulating surface (i.e., the "ball" part of the hip joint). The femoral articulating surface is smooth, and free of muscles and soft tissues. However, the entire femoral head gets resected; so the "first surface" can be used to reference off of the smooth surface (preferably on a remaining non-arthritic portion of the articulating surface), and then guide the attachment of a femoral structure onto the non-resected part of the femur.

Alternatively, the PSF jig 500 may be designed and fabricated to mirror a surface on the femur which has its soft tissues cleared as part of the surgical technique. For example, during an anterior approach to a hip joint, the anterior muscle attachments to the greater trochanter are removed, leaving an area on the bone free of muscle attachments, onto which a PSF jig 500 may be mated via its mirrored mating surface. The pre-operative planning software 102 may consider the surgical technique/approach for the design and fabrication of such a PSF jig 500, and communicate the 3D model(s) 110 accordingly. It will be evident to those skilled in the art, that a patient specific jig intended to mate with a bone at a location which is cleared soft tissues may be applied to various bones (e.g. distal femur, proximal tibia, etc) and types of surgery (e.g. knee replacement surgery).

Figure 6:
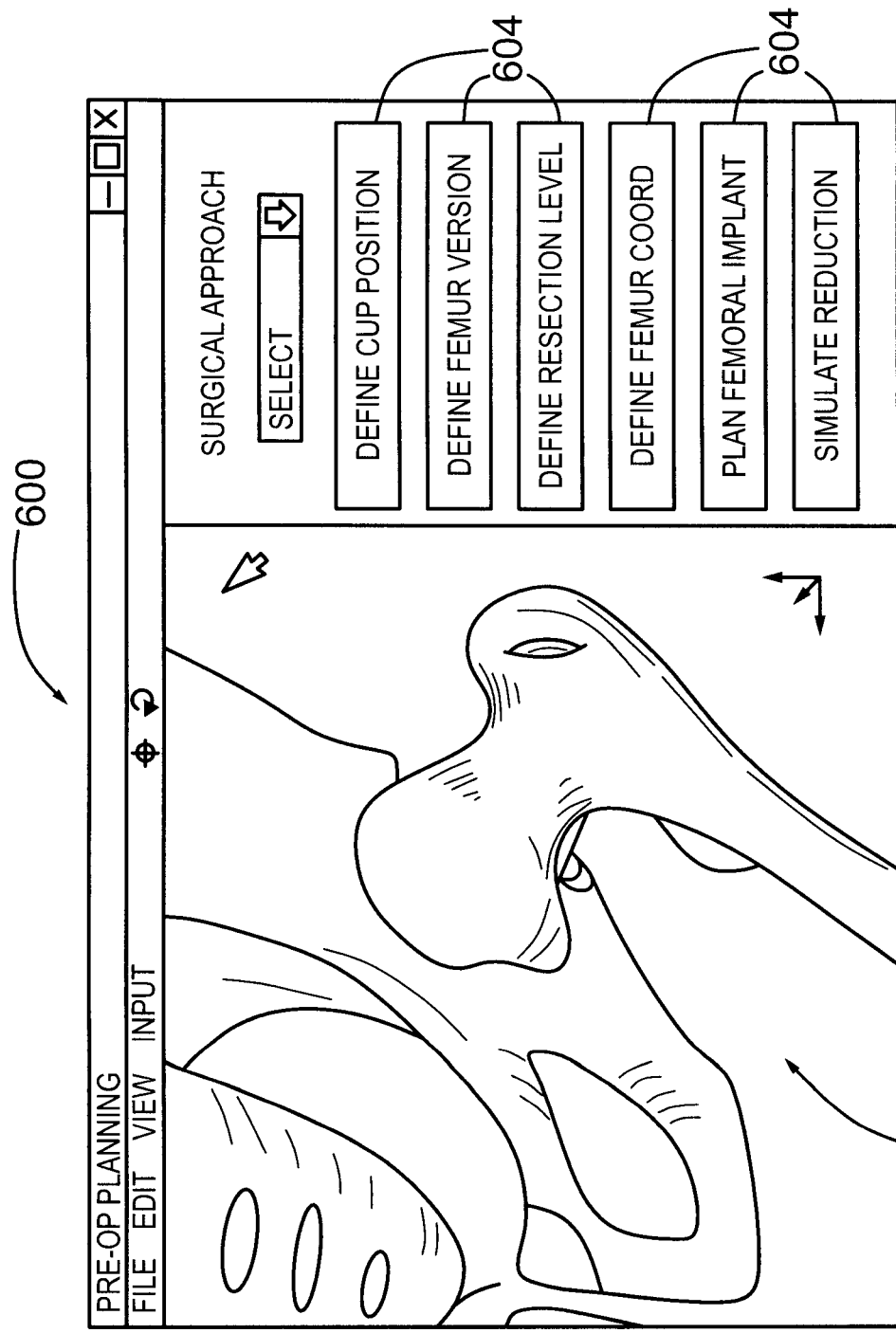
FIG. 6 is a screen-shot of pre-operative planning software, in accordance with one example presented.

FIG. 6 is a screen-shot of pre-operative planning (POP) software 600, in accordance with one example presented. POP software can show a pre-operative 3D image reconstruction 602 of the patient's anatomy. A surgeon may use the POP software to automatically or manually define and/or identify anatomical features of interest to facilitate desired intra-operative positional guidance. In THA, pertinent pre-operative data or features of interest may include: points to define the principle anatomical planes on the pelvis; points to define the principle anatomical planes on the femur; the location of the hip joint COR; the axis defining pre-operative femoral version; points defining the Anterior Pelvic Plane (APP)—e.g., Anterior Superior Iliac Spine, Pubic Tubercles, Pubic Symphysis; the transverse acetabular ligament; features which quantify pelvic tilt; points along femoral axis (anatomical and/or mechanical axis); reference points with respect to pelvis for baseline leg length/offset determination; and/or any other points the surgeon deems pertinent to implant sizing and positioning.

Various functional components 604 can be provided by the POP software. For example, functionality can be provided to: define cup position; define femur version; define resection level; define femur coordinate system; plan femoral implantation; and/or simulate reduction. The POP software 102 may be used to establish the coordinate transformation between the PSA jig and the pelvis. Also, the POP software 102 may be used to determine the pre-operative head center location. Further, the POP software 102 can be used as part of the planning and manufacturing process of the PSA and/or PSF jigs. The patient-specific geometries of the PSA and PSF jigs may be mapped to reference frames (i.e. coordinate systems representative of a patient's anatomy); thus, they may be used to identify the pre-operative relative position of the pelvis and femur. During pre-operative planning of the acetabular component position, the PSA jig may be used to establish a reference map to the angles of abduction and/or anteversion, as well as the native head center position. During pre-operative planning of the femur position, the PSF jig may be used to establish a reference map to directions of leg length, offset, and/or femoral version. The POP software may also take into account the surgical technique (e.g. posterior, Hartinge, mini-incision, direct anterior, etc) which is utilized by the surgeon, as this may influence the preferred shape of the rapidly-manufactured patient-specific jigs 114.

Figure 7:
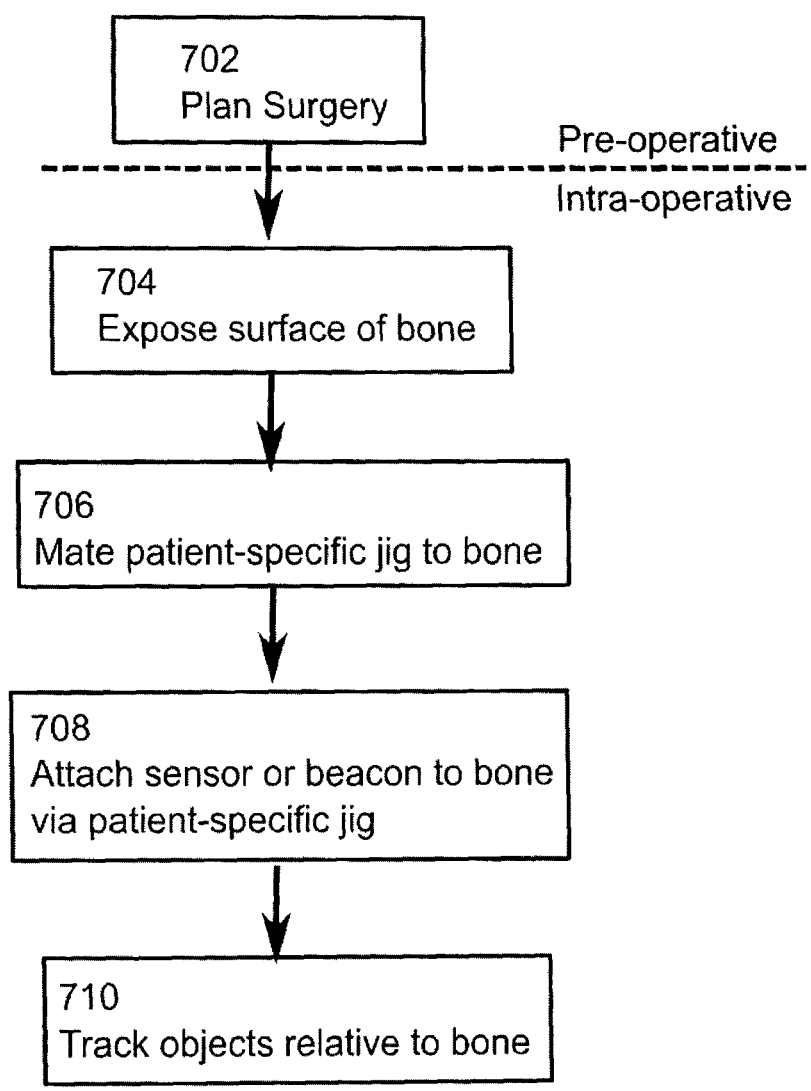
FIG. 7 is a flowchart outlining a method, in accordance with one example presented.

FIG. 7 is a flowchart outlining a method, in accordance with one example presented. In step 702, the pre-operative planning is conducted using the pre-operative planning software 102. As previously discussed, the output of the pre-operative planning may provide pre-operative data (e.g. 3D model data 110) for manufacturing patient specific jigs 114, as well as loading into the intelligent instrumentation system 116. In surgery, step 704 occurs, where the portion of the bone which the PSJ 114 mirrors is exposed. In step 706, the PSJ 114 is mated with the exposed bone in a unique pose, and in step 708, a sensor (e.g. sensor 214) or a beacon (e.g. beacon 208) is rigidly attached to the bone with a unique pose, imposed/constrained by the PSJ 114. In step 710, an intelligent instrumentation system tracks the pose of at least one object; the tracking is inherently relative to the bone, since the pre-operative data is utilized.

Figure 8:
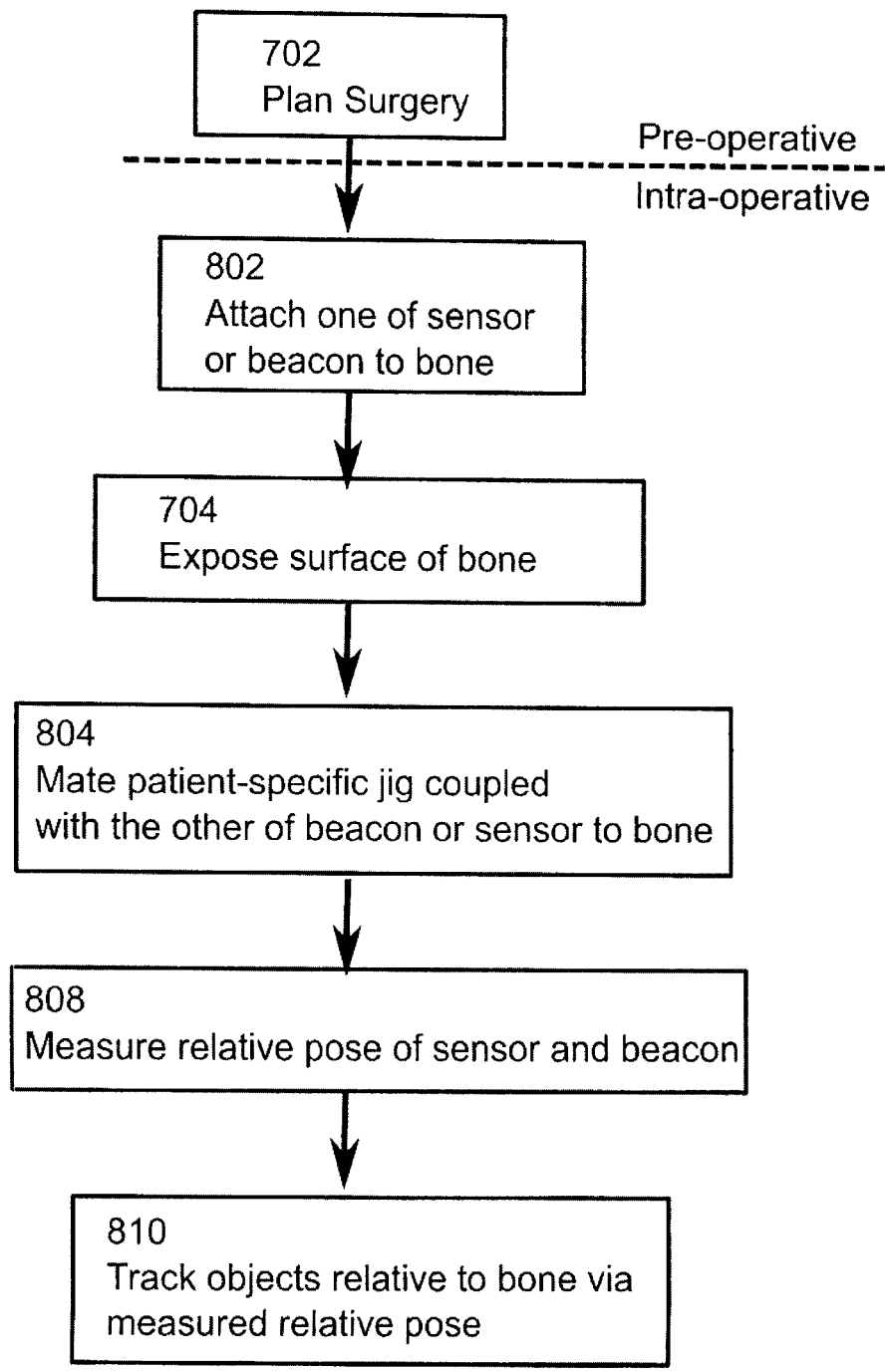
FIG. 8 is a flowchart outlining a method, in accordance with another example presented.

FIG. 8 is a flowchart outlining a method, in accordance with one example presented. Steps 702 and 704 are identical to the corresponding steps in FIG. 7. In step 802, a sensor (e.g. sensor 214) or a beacon (e.g. beacon 208) is rigidly attached to the bone (which the PSJ 114 mirrors), with an arbitrary pose. In step 804, the PSJ 114 is mated with the exposed bone in a unique pose, and coupled with the other of a sensor (e.g. sensor 214) or a beacon (e.g. beacon 208) to what was attached in step 802. A relative pose measurement is captured between the sensor and beacon (where one is rigidly mounted to the bone, and the other is coupled to a PSJ, mated with a bone) in step 808. Afterwards, in step 810, an intelligent instrumentation system tracks the pose of at least one object; the tracking is relative to the bone via the relative pose captured in the measurement of step 808, and also utilizes the pre-operative data.

Figure 9:
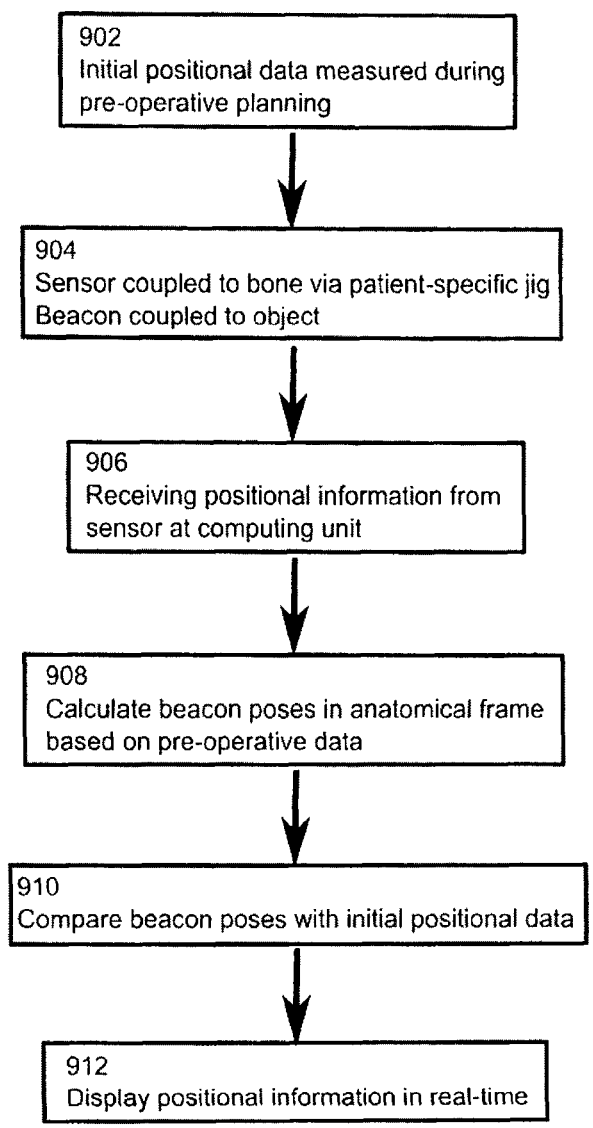
FIG. 9 is a flowchart outlining a method, in accordance with another example presented.

In FIG. 9, a computer implemented method for tracking intra-operatively an object using a sensor (e.g. bone, instrument, implant, etc) is presented according to one example. In step 904, the sensor is configured to receive positional signals from a beacon, the sensor coupled to a first bone in a predetermined pose in an anatomical coordinate frame via a patient-specific jig (PSJ), and the beacon is coupled to the object, which object comprises one of a second bone and a surgical tool. In step 906, an intra-operative computing unit (in communication with the sensor) receives positional information from the sensor. In step 908, beacon poses are calculated with respect to the anatomical coordinate frame utilizing pre-operative data representing the PSJ. In step 912, the positional information for the object is displayed in real time. Optionally, during pre-operative planning, initial positional data (e.g. initial leg length, initial hip COR location) is measured using the pre-operative planning software (step 902), and the method comprises comparing the calculated poses with the initial positional data (step 910) (e.g. calculating and displaying change in leg length).

Figure 10:
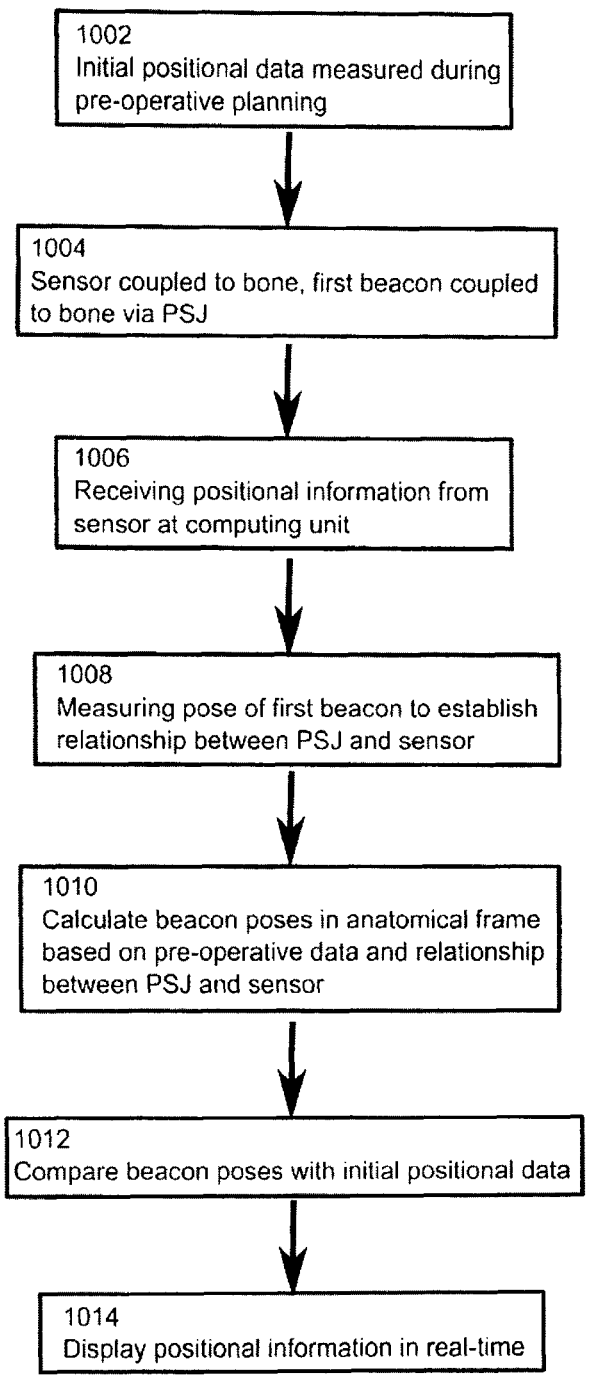
FIG. 10 is a flowchart outlining a method, in accordance with another example presented.

In FIG. 10, a computer implemented method for tracking intra-operatively an object using a sensor (e.g. bone, instrument, implant, etc) is presented according to one example. In step 1004, the sensor is configured to receive positional signals from a first beacon and a second beacon, the sensor coupled to a first bone, the first beacon is coupled to the first bone via a patient specific jig configured to mate with the first bone, and the second beacon is coupled to the object, which comprises one of a second bone and a surgical tool. In step 1006, an intra-operative computing unit (in communication with the sensor) receives positional information from the sensor. In step 1008, a pose of the first beacon when coupled to the first bone via the PSJ to establish a positional relationship between the sensor and the PSJ is measured. In step 1010, beacon poses are calculated with respect to the anatomical coordinate frame utilizing pre-operative data representing the PSJ, as well as the positional relationship between the sensor and the PSJ. In step 1014, the positional information for the object is displayed in real time. Optionally, during pre-operative planning, initial positional data (e.g. initial leg length, initial hip COR location) is measured using the pre-operative planning software (step 1002), and the method comprises comparing the calculated poses with the initial positional data (step 1012) (e.g. calculating and displaying change in leg length).

Figure 11:
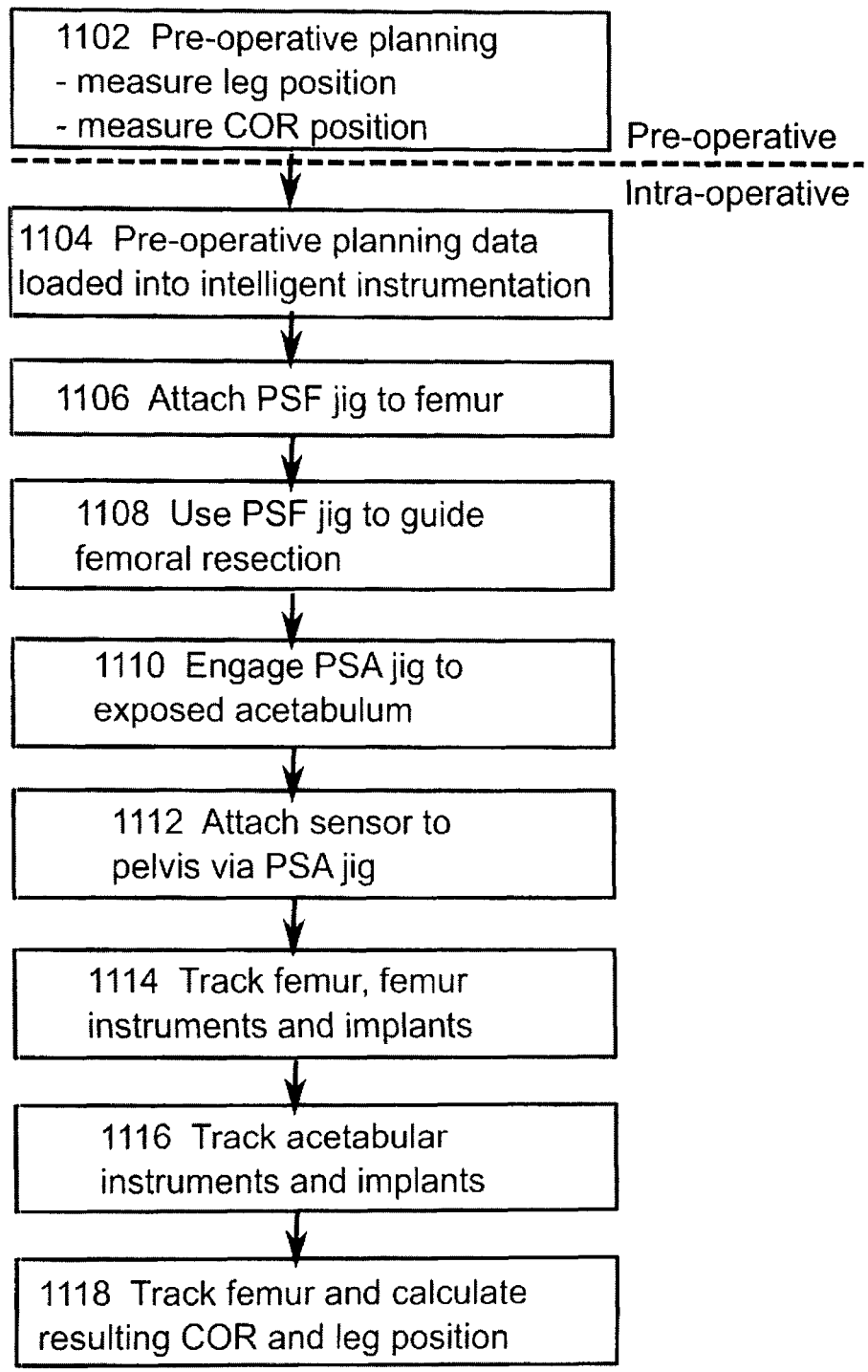
FIG. 11 is a flowchart outlining a method, in accordance with another example presented.

FIG. 11 is a flowchart outlining a method with application to THA. Prior to surgery, in step 1102. POP software may be used to determine, inter alia, the initial/baseline leg position (i.e. leg length, offset, AP position), and the initial hip center of rotation position. In step 1104, POP software data output (e.g. pre-operative data output 110) is loaded into intra-operative software (e.g. in intelligent instrumentation system 116). In step 1106, prior to hip dislocation, but after joint exposure, the PSF jig 206 is attached to the femur. In step 1108, the PSF jig is used to guide femoral head resection. In step 1110, the PSA jig is engaged to the exposed acetabulum. In step 1112, the PSA jig is used to guide the rigid mounting structure (e.g. fixation screws/pins 210) into the pelvis 204, used to mount the sensor. When mounted, the sensor may be considered "inherently registered" to the pelvis. In step 1114, during broaching and prosthesis implantation, the positional relationship between broach/prosthesis and femur sensor unit is tracked and information (e.g., femoral version) is provided to the surgeon. In step 1116, during acetabular reaming, the reamer is tracked, and reaming information (e.g. depth, angle) is provided to the surgeon. Additionally, during this step, the acetabular impactor is tracked and cup positional information (e.g., abduction, anteversion, combined anteversion) is provided to the surgeon. In step 1118, the new hip COR position, and the new leg length/offset are measured using the intelligent instrumentation, and changes (from initial) may be calculated and provided to the surgeon.

Figure 12:
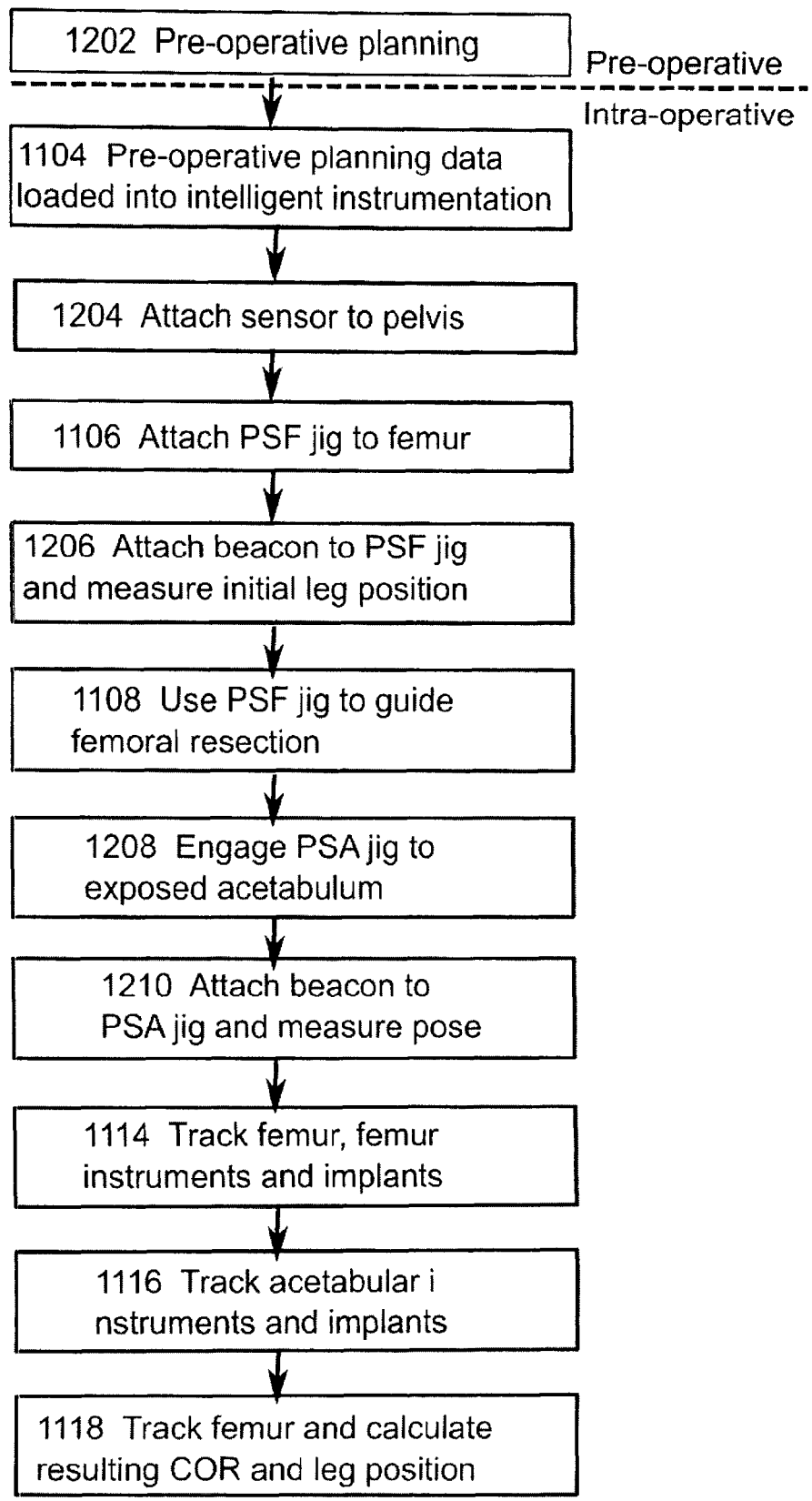
FIG. 12 is a flowchart outlining a method, in accordance with another example presented.

FIG. 12 is a flowchart outlining a method, in accordance with another example presented. Prior to surgery, in step 1202, POP software is used, but not necessarily to measure an initial leg position. Steps 1104, 1106, 1108, 1114, 1116 and 1118 may be used in the method of FIG. 12. In step 1204, prior to hip dislocation, a pelvis sensor is attached to the pelvis, not necessarily in a pre-determined pose. In step 1206, after the PSF jig is attached, but prior to dislocation, the pre-dislocation femur position is measured using a beacon (e.g. beacon 208) on the PSF jig and a sensor (e.g. sensor 214) on the pelvis. In step 1208, the PSA jig is engaged to the exposed acetabulum. In step 1210, a beacon is attached to the PSA jig to take a pose measurement to relate the pelvis pose to the sensor pose. The PSA jig is then disengaged from the acetabular surface. In this case, the sensor is not "inherently registered" to the pelvis; however, registration is effectively achieved using a single-measurement.

Figure 13:
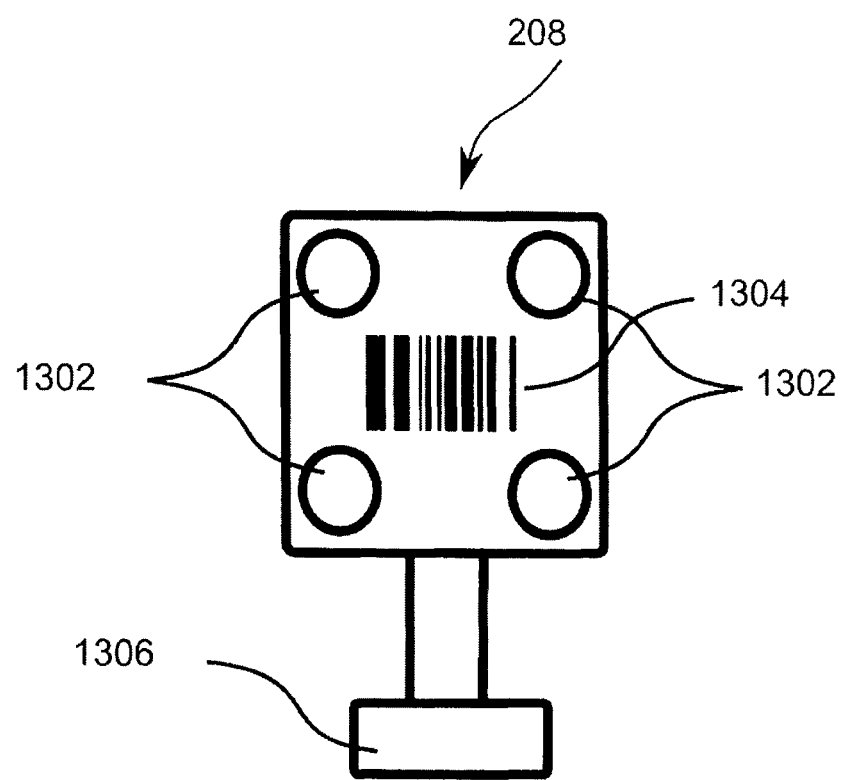
FIG. 13 is a illustration of a beacon with a verification feature, in accordance with one example presented.

With reference to the block diagram of FIG. 1, the surgery 120 typically occurs several weeks after the pre-operative planning (using the POP software 102). Due to the complexities of hospital processes and jig manufacturing logistics, there may be a risk that patient specific jigs get mixed up, and the wrong jigs are used in surgery for a particular patient. To mitigate this risk, a verification feature may be associated with the jigs. This verification process may involve providing the intra-operative computing unit of the intelligent instrumentation 116 with a verification code (along with the transfer of the 3D model information 110), and associating a corresponding verification code with the patient specific jigs 114. Prior to surgery, the intelligent instrumentation computing platform cross-checks the verification codes (e.g. checksum, cyclic redundancy check, etc) to ensure that the patient specific jigs 114 and 3D model 110 match the patient. The patient specific jigs may be encoded with pre-operative verification information (e.g. a verification code) in several ways. In FIG. 13, a beacon 208 (with optically detectable markers 1302), rapidly manufactured along with the patient specific jigs, has a barcode verification feature 1304, which may be optically readable by the sensor 214. Rather than a separate feature, the verification may be accomplished by using a patient-specific positional pattern of markers 1302 on the beacon 1300, such that the intelligent instrumentation system will no generate valid pose data if the correct marker 1302 configuration is not present. Alternatively, an optically readable verification feature may be included on the patient specific jig or the patient specific jig packaging and/or labeling. An optically readable verification feature (e.g. barcode, 2D barcode, relative position of markers 1302, etc) may be read by an optical sensor unit, or by the intra-operative computing unit 216 (e.g. via a webcam). Alternatively, the beacon 1300 and/or patient specific jigs may be themselves encoded with the necessary 3D Model 110 information (e.g. via feature 1304), readable by the intelligent instrumentation system 116 thus obviating the need for the data transfer of the 3D Model 110 from the POP software 102 to the intra-operative computing unit of the intelligent instrumentation system 116. The 3D model information required by the intelligent instrumentation system may be one or more pose data (e.g. rotation matrix and vector), which represents a mapping from a patient-specific jig coordinate frame to an anatomical coordinate frame.

ADDITIONAL EXAMPLES

In one example, there is provided a system for performing a hip replacement surgery, comprising: a pelvis sensor unit; a femur sensor unit; a tool sensor unit configured to be coupled to an acetabular tool; a patient-specific acetabular jig having a first surface and a second surface, wherein the first surface is pre-operatively formed to mirror an acetabular surface of the patient; and a patient-specific femoral jig having a first surface and a second surface, wherein the first surface is pre-operatively formed to mirror a femoral surface of the patient, and wherein the second surface has a coupling interface for operatively coupling the femur sensor unit to the patient-specific femoral jig. The system for includes a computer-readable storage medium having instructions executable by at least one processing device that, when executed, cause the processing device to: (a) determine, calculate, or otherwise identify a position of the pelvis sensor unit; (b) determine, calculate, or otherwise identify a position of the femur sensor unit; (c) track a relative position and/or orientation of the acetabular tool during an implantation procedure, based on a positional relationship between the pelvis sensor unit and the tool sensor unit; (d) calculate angles of abduction and/or anteversion based on the position and/or orientation of the acetabular tool; (e) provide a real-time display conveying the angles of abduction and/or anteversion during the implantation procedure; (f) measure a post-reduction positional relationship between the pelvis sensor unit and the femur sensor unit; (g) determine, calculate, or otherwise identify a change in leg position based on the post-reduction positional relationship between the pelvis sensor unit and the femur sensor unit; and (h) display the change in leg position. The computer-readable storage medium may further include instructions executable by at least one processing device that, when executed, cause the processing device to: track a femur orientation during a leg positioning procedure based on a positional relationship between the pelvis sensor unit and the femur sensor unit; and provide a real-time display conveying the femur orientation during the leg positioning procedure.

The pelvis sensor unit may be configured to be operatively coupled to a patient's pelvis. The pelvis sensor unit may alternatively be configured to be operatively coupled to the patient-specific acetabular jig. The second surface of the patient-specific acetabular jig may be configured to guide, or otherwise facilitate, the operative coupling of the pelvis sensor to the pelvis. The position of the pelvis sensor may be determined, calculated, or otherwise identified based in part by a positional relationship between the first surface and the second surface of the patient-specific acetabular jig. The position of the pelvis sensor may be determined, calculated, or otherwise identified based in part on a pre-operative three-dimensional image reconstruction of the patient's acetabulum.

The position of the femur sensor may be determined, calculated, or otherwise identified based in part by a positional relationship between the first surface and the second surface of the patient-specific femoral jig. The position of the femur sensor may alternatively be determined, calculated, or otherwise identified based in part on a pre-operative formation of the patient-specific femoral jig. The change in leg position may be determined, calculated, or otherwise identified based in part on the a pre-operative three-dimensional image reconstruction of the patient's pelvis and femur. The change in leg position includes a leg length measurement, an offset measurement, and/or an anterior-posterior position measurement. A pre-operative center-of-rotation is determined, calculated, or otherwise identified based on a pre-operative three-dimensional image reconstruction of the patient's acetabular surface.

The first surface of the patient-specific acetabular jig may be opposite the second surface. The first surface of the patient-specific acetabular jig may be formed based on a pre-operative three-dimensional image reconstruction of the patient's acetabular surface. The first surface of the patient-specific femoral jig may be pre-operatively formed based on a pre-operative three-dimensional image reconstruction of the patient's femoral surface.

In one example, there is provided a system for performing a hip replacement surgery, comprising: a pelvis sensor unit configured to be operatively coupled to a patient's pelvis; a patient-specific acetabular jig having a first surface and a second surface, wherein the first surface is pre-operatively formed to mirror an acetabular surface of the patient; and a reference sensor unit. The system further includes a computer-readable storage medium having instructions executable by at least one processing device that, when executed, cause the processing device to: (a) determine, calculate, or otherwise identify a position of the pelvis sensor unit; (b) track an orientation of an acetabular tool during an implantation procedure based on a positional relationship between the pelvis sensor unit and the reference sensor unit, wherein the reference sensor unit is coupled to the acetabular tool during the implantation procedure; (c) determine, calculate, or otherwise identify implant parameters based on the orientation of the acetabular tool; and (d) provide a real-time display of the implant parameters during the implantation procedure. The computer-readable storage medium may further include instructions executable by at least one processing device that, when executed, cause the processing device to: (e) measure a post-reduction leg position based on a post-reduction positional relationship between the pelvis sensor unit and the reference sensor unit, wherein the reference sensor unit is coupled to the patient's femur; (f) determine, calculate, or otherwise identify a change in leg position based in part on the post-reduction leg position; and (g) provide a display of the change in leg position.

The first surface of the patient-specific acetabular jig may be formed based on a pre-operative three-dimensional image reconstruction of the patient's acetabular surface. The second surface of the patient-specific acetabular jig may be configured to guide, or otherwise facilitate, the operative coupling of the pelvis sensor to the pelvis.

The position of the pelvis sensor unit may be determined, calculated, or otherwise identified based in part on a positional relationship between the pelvis sensor unit and the reference sensor unit, wherein the reference sensor unit is coupled to the second surface of the patient-specific acetabular jig. The position of the pelvis sensor unit may alternatively be determined, calculated, or otherwise identified based in part on a pre-operative three-dimensional image reconstruction of the patient's acetabular surface.

In another example, there is provided a system for performing a hip replacement surgery, comprising: a pelvis sensor unit configured to be coupled to a patient's pelvis; a reference sensor unit; a patient-specific acetabular jig having a first surface and a second surface, wherein the first surface is pre-operatively formed to mirror an acetabular surface of the patient, based on a pre-operative three-dimensional image reconstruction of the patient's acetabular surface, and wherein the second surface has a coupling interface for operatively coupling the reference sensor unit to the patient-specific acetabular jig; and a patient-specific femoral jig having a first surface and a second surface, wherein the first surface is pre-operatively formed to mirror a femoral surface of the patient, based on a pre-operative three-dimensional image reconstruction of the patient's femoral surface, and wherein the second surface has a coupling interface for operatively coupling the reference sensor unit to the patient-specific femoral jig. The system further includes a computer-readable storage medium having instructions executable by at least one processing device that, when executed, cause the processing device to: (a) determine, calculate, or otherwise identify a position of the pelvis sensor unit based on: 1) the pre-operative three-dimensional image reconstruction of the patient's acetabular surface and 2) a positional relationship between the pelvis sensor and the reference sensor, when the reference sensor is coupled to the second surface of the patient-specific acetabular jig; (b) determine, calculate, or otherwise identify an initial leg position based on an initial positional relationship measurement between the pelvis sensor unit and the reference sensor unit, when the reference sensor unit is coupled to the patient-specific femoral jig; (c) measure a post-reduction leg position based on a positional relationship between the pelvis sensor unit and the reference sensor unit, when the reference sensor unit is coupled to the patient-specific femoral jig; (d) calculate a change in leg position between the initial leg position and the post-reduction leg position; and (e) provide a display of the change in leg position. The computer-readable storage medium may further include instructions executable by at least one processing device that, when executed, cause the processing device to: track a femur orientation during a leg positioning procedure based on a positional relationship between the pelvis sensor unit and the reference sensor unit, when the reference sensor unit is coupled to the patient-specific femoral jig; and provide a real-time display conveying the femur orientation during the leg positioning procedure. The computer-readable storage medium may further includes instructions executable by at least one processing device that, when executed, cause the processing device to calculate a center-of-rotation of the patient's femur. A pre-operative center-of-rotation may be determined, calculated, or otherwise identified based on the pre-operative three-dimensional image reconstruction of the patient's acetabular surface.

In still another example, there is provided a system for performing a computer-assisted hip replacement surgery, comprising: a pelvis sensor unit configured to be coupled to a patient's pelvis; a femur sensor unit; and a patient-specific femoral jig having a first surface and a second surface, wherein the first surface is pre-operatively formed to mirror a femoral surface of the patient, based on a pre-operative three-dimensional image reconstruction of the patient's femoral surface, and wherein the second surface has a coupling interface for operatively coupling the femur sensor to the patient-specific femoral jig. The system further includes a computer-readable storage medium having instructions executable, by at least one processing device: (a) which when executed prior to a dislocation of the femur from the pelvis, wherein the pelvis sensor unit is coupled to the pelvis and the femur sensor unit is coupled to the patient-specific femoral jig, cause the processing device to measure a pre-dislocation positional relationship between the pelvis sensor unit and the femur sensor unit, and (b) which when executed after the femur has been reduced, cause the processing device to (1) measure a post-reduction positional relationship between the pelvis sensor unit and the femur sensor unit and (2) calculate and display a change in leg length, a change in offset, and/or change in anterior-posterior position based on the pre-dislocation positional relationship and the post-reduction positional relationship. The system may further comprising a computer-readable storage medium having instructions executable, by at least one processing device, which when executed during a reduction procedure, wherein the pelvis sensor unit is coupled to the pelvis and the femur sensor unit is coupled to the patient-specific femoral jig, cause the processing device to display a reduction orientation of the femur.

In another example, there is provided a method of performing joint-replacement surgery, comprising: (a) performing a pre-operative three-dimensional image reconstruction of a patient's joint and surrounding areas; (b) determining pre-operative positions of the joint and surrounding anatomical structures; (c) loading pre-operative data into an intra-operative surgical navigation software package; (d) attaching a first patient-specific jig to a surrounding anatomical structure, wherein the first patient-specific jig includes a first surface and a second surface, wherein the first surface is pre-operatively formed to mirror a surface of the patient's anatomical structure, and wherein the second surface has a coupling interface for operatively coupling a first sensor unit to the first patient-specific jig; (e) using the first patient-specific jig to guide resection of the anatomical structure; (f) attaching a second patient-specific jig to a joint surface, wherein the second patient-specific jig includes a first surface and a second surface, wherein the first surface is pre-operatively formed to mirror the joint surface, and wherein the second surface has a guide interface; (g) using the guide interface on the second patient-specific jig to guide the coupling of a second sensor unit to the joint surface; (h) positioning a prosthesis in, on, or around the anatomical structure; (i) measuring a positional relationship between the first sensor unit and the second sensor unit during an implantation procedure; (j) measuring a post-implantation positional relationship between the first sensor unit and the second sensor unit; and (k) calculating and providing the differences between the pre-operative positions and the post-implantation positional relationship. The joint may be the patient's hip, knee, ankle, or shoulder. The joint may be the patient's hip, and the pre-operative determination of the joint and surrounding anatomical structures includes determining pre-operative leg length.

The pre-operative data may include the pre-operative three-dimensional image reconstruction and the pre-operative positions of the joint and surrounding anatomical structures. The pre-operative data may also include anatomical parameters selected from the group consisting of: points to define the principle anatomical planes on the pelvis; points to define the principle anatomical planes on the femur; the location of the hip joint center-of-rotation (COR); axis defining pre-operative femoral version; points defining the anterior pelvic plane (APP), anterior superior iliac spine, pubic tubercles, pubic symphysis; transverse acetabular ligament; features which quantify pelvic tilt; points along femoral axis (anatomical and/or mechanical axis); reference points with respect to pelvis for baseline leg length/offset determination; any anatomical points defined or identified by a surgeon; and/or any equivalents or combinations thereof.

In another example, there is provided a method of performing joint-replacement surgery, comprising: (a) performing a pre-operative three-dimensional image reconstruction of a patient's joint and surrounding areas; (b) determining pre-operative positions of the joint and surrounding anatomical structures; (c) loading pre-operative data into an intra-operative surgical navigation software package; (d) attaching a reference sensor unit to a first surrounding anatomical structure; (e) attaching a first patient-specific jig to a second surrounding anatomical structure, wherein the first patient-specific jig includes a first surface and a second surface, wherein the first surface is pre-operatively formed to mirror a surface of the patient's second surrounding anatomical structure, and wherein the second surface has a first coupling interface for operatively coupling a first sensor unit to the first patient-specific jig; (t) measuring a pre-dislocation positional relationship between the reference sensor and the first sensor; (g) using the first patient-specific jig to guide resection of the second surrounding anatomical structure; (h) attaching a second patient-specific jig to a joint surface, wherein the second patient-specific jig includes a first surface and a second surface, wherein the first surface is pre-operatively formed to mirror the joint surface, and wherein the second surface has a second coupling interface for operatively coupling a second sensor unit to the second patient-specific jig; (i) measuring a positional relationship between the second sensor and the reference sensor; (j) positioning a prosthesis in, on, or around the anatomical structure; (k) measuring a positional relationship between the first sensor unit and the reference sensor unit during an implantation procedure; (l) measuring a post-implantation positional relationship between the first sensor unit and the reference sensor unit; and (m) calculating and providing the differences between the pre-operative positions and the post-implantation positional relationship. The joint may be the patient's hip, knee, ankle, or shoulder.

The pre-operative data may include the pre-operative three-dimensional image reconstruction and the pre-operative positions of the joint and surrounding anatomical structures. The pre-operative data may also include anatomical parameters selected from the group consisting of: points to define the principle anatomical planes on the pelvis; points to define the principle anatomical planes on the femur; the location of the hip joint center-of-rotation (COR); axis defining pre-operative femoral version; points defining the anterior pelvic plane (APP), anterior superior iliac spine, pubic tubercles, pubic symphysis; transverse acetabular ligament; features which quantify pelvic tilt; points along femoral axis (anatomical and/or mechanical axis); reference points with respect to pelvis for baseline leg length/offset determination; any anatomical points defined or identified by a surgeon; and/or any equivalents or combinations thereof.

In yet another example, there is provided a method of performing hip replacement surgery, comprising: (a) pre-operative planning to define PSA and PSF jig geometries, and/or desired implant positioning; (b) (optionally) attach a pelvis pin and pelvis sensor unit to the iliac crest; (c) performing an incision to expose the joint; (d) attaching the PSF jig to the femur; (e) measuring a pre-dislocation femur position using the sensor unit on the PSF jig and pelvis sensor on pelvis; (f) dislocating the joint; (g) resecting the femoral head using the PSF jig for reference; (h) tracking a femoral broach with respect to the femur sensor unit during a femoral broaching procedure to affect desired post-operative femoral version; (i) implanting a femoral prosthesis; (j) (optionally) tracking an insertion tool to verify and store the post-operative femoral version; (k) engaging the PSA jig to the acetabulum; (l) measuring the PSA jig position, using the sensor unit on the PSA jig and pelvis sensor unit on the pelvis; (m) removing and discarding the PSA jig; (n) reaming the acetabulum under guidance for angles/depth; (o) impacting prosthetic cup under guidance for angles (referring to femoral version for combined anteversion); (p) (optionally) performing a trial reduction; (q) articulating the femur within the joint; (r) calculating the change in head center location as well as change in leg length and offset (e.g., based on initial leg length measurement); (s) repeating the articulation when the cup/liner is changed; (t) calculating the leg length/offset during trialing/final prosthesis without articulation, when the cup/liner are unchanged; (u) performing a final reduction; and/or (v) removing and discarding the PSF jig.

In still another example, there is provided a computer-implemented hip replacement surgery system, comprising: a patient-specific acetabular jig having a surface pre-operatively formed to mirror an acetabular surface of a patient; a pelvis sensor configured to be operatively coupled to a patient's pelvis via the patient-specific acetabular jig; a patient-specific femoral jig having a surface pre-operatively formed to mirror a femoral surface of the patient; a femur sensor configured to be operatively coupled to the patient-specific femoral jig; and an intra-operative computing system configured to measure pre- and post-reduction positional relationships between the pelvis sensor and the femur sensor, and provide a display of operative parameters based on the pre- and/or post-reduction positional relationships.

The system may further comprise a pre-operative computing system for creating a three-dimensional image reconstruction of the pelvis and femur. The intra-operative computing unit system may be configured to display the three-dimensional image reconstruction of the pelvis and the femur. The pre-operative computing system may be used to prepare a pre-operative hip replacement plan. The intra-operative computing system may allow the surgeon to adjust the pre-operative hip replacement plan. The intra-operative computing system and the pre-operative computing system may comprise the same hardware. The patient-specific femoral jig may include a resection surface to guide resection of the patient's femur.

In one example, there is provided a patient-specific femoral jig, comprising: a first surface pre-operatively formed to mirror a surface of the patient's femur; a second surface having a coupling interface for operatively coupling to a sensor unit; and a third surface to guide resection of the patient's femur.

In another example, there is provided a patient-specific acetabular jig, comprising: a first surface pre-operatively formed to mirror a surface of the patient's acetabulum; and a second surface having a coupling interface for operatively coupling to a sensor unit.

In still another example, there is provided a patient-specific acetabular jig, comprising: a first surface pre-operatively formed to mirror a surface of the patient's acetabulum; and a second surface having an integrally formed sensor unit.

In another example, there is provided a method for facilitating a computer-assisted joint replacement surgery, comprising: (a) performing a pre-operative image scan of the joint and surrounding anatomical structures; (b) deriving a three-dimensional image reconstruction of the joint and at least one surrounding anatomical structures; (c) manufacturing a patient-specific jig for mounting on the least one anatomical structure, based on the three-dimensional image reconstruction; (d) exposing the joint and the at least one surrounding anatomical structure; (e) attaching a reference sensor unit to a fixed anatomical structure; (f) attaching the patient-specific jig to the at least one surrounding anatomical structure; (g) attaching a tracking sensor unit to the patient-specific jig; (h) determining a pre-operative relative position between the fixed anatomical structure and the at least one surrounding anatomical structure based on the relative position between the reference sensor unit and the tracking sensor unit; (i) dislocating the at least one surrounding anatomical structure from the joint; (j) inserting an implant and/or prosthesis in the joint and/or the at least one surrounding anatomical structure; (k) tracking the relative position of the at least one surrounding anatomical structure during a reduction procedure; (l) calculating a change in pre-operative relative position versus post-operative relative position between the fixed anatomical structure and the at least one surrounding anatomical structure; and (m) displaying the change in relative position. The joint may be the hip joint and the at least one surrounding anatomical structure is the femur. The fixed anatomical structure may be the pelvis. The three-dimensional image reconstruction may employ a CT scan, MRI, and/or X-ray images. The manufacturing step may be performed by rapid-manufacturing of the patient-specific jig.

In another example, there is provided a method of performing hip replacement surgery, comprising tracking the relative position between a femur sensor unit and a reference sensor unit, wherein the femur sensor unit is coupled to a patient-specific femoral jig, which in turn is attached to a patient's femur, and wherein the reference sensor unit is coupled to the patient's pelvis. The relative position of the reference sensor may be determined based on a pre-operative three-dimensional image reconstruction of the patient's pelvis. A patient-specific acetabular jig may be used to determine the relative position of the reference sensor.

Computer Implementation.

Figure 14:
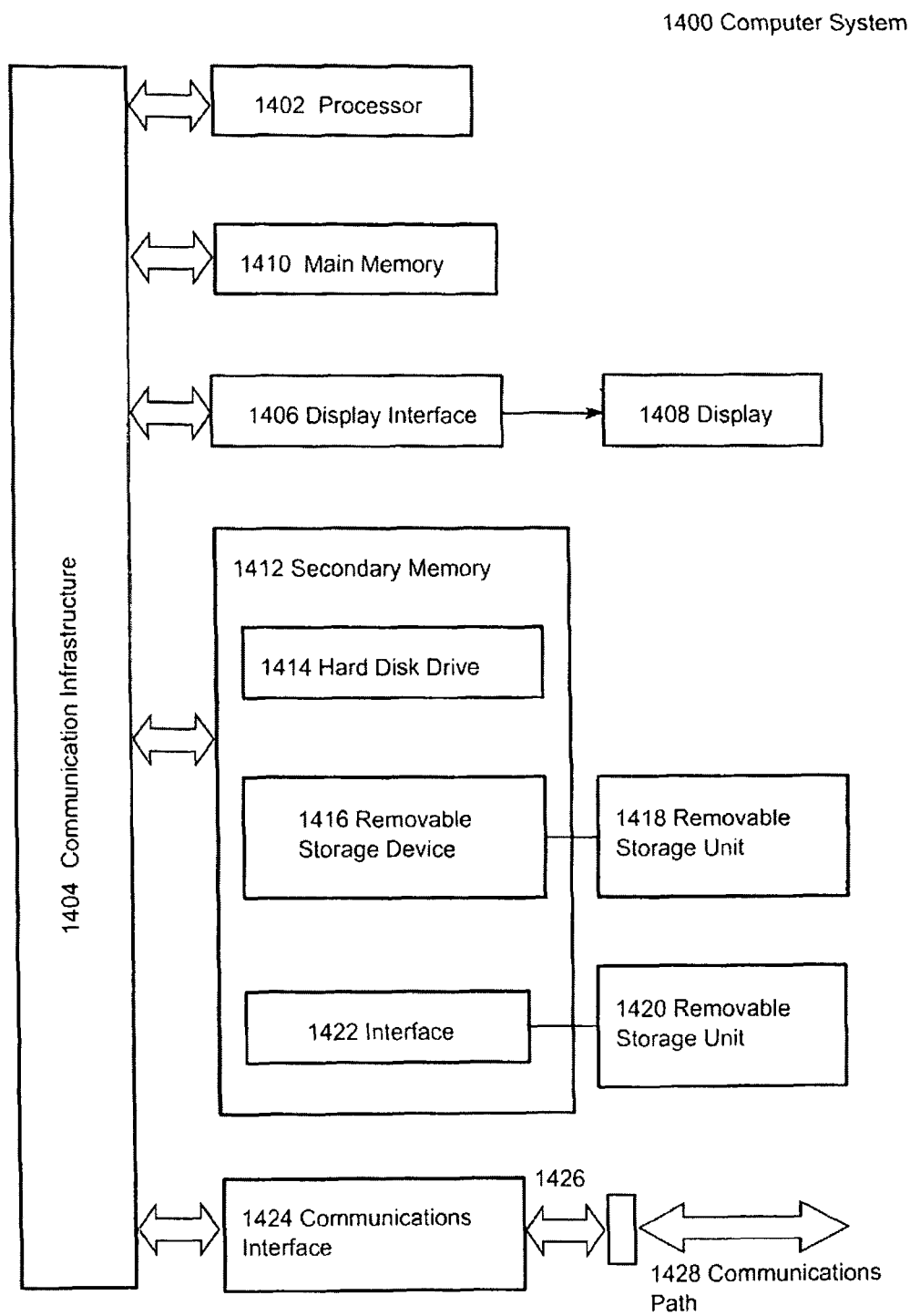
FIG. 14 is a schematic drawing of a computer system used to implement the methods presented.

In one example, there is provided one or more computer systems capable of carrying out the functionality described herein. For example, FIG. 14 is a schematic drawing of a computer system 1400 used to implement the methods presented above. Computer system 1400 includes one or more processors, such as processor 1402. The processor 1402 is connected to a communication infrastructure 1404 (e.g., a communications bus, cross-over bar, or network). Computer system 1400 can include a display interface 1406 that forwards graphics, text, and other data from the communication infrastructure 1404 (or from a frame buffer not shown) for display on a local or remote display unit 1408.

Computer system 1400 also includes a main memory 1410, such as random access memory (RAM), and may also include a secondary memory 1412. The secondary memory 1412 may include, for example, a hard disk drive 1414 and/or a removable storage drive 1416, representing a floppy disk drive, a magnetic tape drive, an optical disk drive, flash memory device, etc. The removable storage drive 1416 reads from and/or writes to a removable storage unit 1418. Removable storage unit 1418 represents a floppy disk, magnetic tape, optical disk, flash memory device, etc., which is read by and written to by removable storage drive 1416. As will be appreciated, the removable storage unit 1418 includes a computer usable storage medium having stored therein computer software, instructions, and/or data.

In alternative examples, secondary memory 1412 may include other similar devices for allowing computer programs or other instructions to be loaded into computer system 1400. Such devices may include, for example, a removable storage unit 1420 and an interface 1422. Examples of such may include a program cartridge and cartridge interface (such as that found in video game devices), a removable memory chip (such as an erasable programmable read only memory (EPROM), or programmable read only memory (PROM)) and associated socket, and other removable storage units 1420 and interfaces 1422, which allow computer software, instructions, and/or data to be transferred from the removable storage unit 1420 to computer system 1400.

Computer system 1400 may also include a communications interface 1424. Communications interface 1424 allows computer software, instructions, and/or data to be transferred between computer system 1400 and external devices. Examples of communications interface 1424 may include a modem, a network interface (such as an Ethernet card), a communications port, a Personal Computer Memory Card International Association (PCMCIA) slot and card, etc. Software and data transferred via communications interface 1424 are in the form of signals 828 which may be electronic, electromagnetic, optical or other signals capable of being received by communications interface 1424. These signals 1426 are provided to communications interface 1424 via a communications path (e.g., channel) 1428. This channel 1428 carries signals 1426 and may be implemented using wire or cable, fiber optics, a telephone line, a cellular link, a radio frequency (RF) link, a wireless communication link, and other communications channels.

In this document, the terms "computer-readable storage medium," "computer program medium," and "computer usable medium" are used to generally refer to media such as removable storage drive 1416, removable storage units 1418, 1420, data transmitted via communications interface 1424, and/or a hard disk installed in hard disk drive 1414. These computer program products provide computer software, instructions, and/or data to computer system 1400. These computer program products also serve to transform a general purpose computer into a special purpose computer programmed to perform particular functions, pursuant to instructions from the computer program products/software. Examples are directed to such computer program products.

Computer programs (also referred to as computer control logic) are stored in main memory 1410 and/or secondary memory 1412. Computer programs may also be received via communications interface 1424. Such computer programs, when executed, enable the computer system 1400 to perform the features as discussed herein. In particular, the computer programs, when executed, enable the processor 1402 to perform the features of the presented methods. Accordingly, such computer programs represent controllers of the computer system 1400. Where appropriate, the processor 1402, associated components, and equivalent systems and subsystems thus serve as "means for" performing selected operations and functions. Such "means for" performing selected operations and functions also serve to transform a general purpose computer into a special purpose computer programmed to perform said selected operations and functions.

In an example such as one implemented using software, the software may be stored in a computer program product and loaded into computer system 1400 using removable storage drive 1416, interface 1422, hard drive 1414, communications interface 1424, or equivalents thereof. The control logic (software), when executed by the processor 1402, causes the processor 1402 to perform the functions and methods described herein.

In another example, the methods are implemented primarily in hardware using, for example, hardware components such as application specific integrated circuits (ASICs). Implementation of the hardware state machine so as to perform the functions and methods described herein will be apparent to persons skilled in the relevant art(s). In yet another example, the methods are implemented using a combination of both hardware and software.

Examples, including any systems and methods described herein, may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing firmware, software, routines, instructions, etc.

In one example, data communication between the system components is accomplished over a network consisting of electronic devices connected either physically or wirelessly, wherein data is transmitted from one device to another. Such devices (e.g., end-user devices) may include, but are not limited to: a desktop computer, a laptop computer, a handheld device or PDA, a cellular telephone, a set top box, an television system, a mobile device or tablet, or systems equivalent thereto. Exemplary networks include a Local Area Network, a Wide Area Network, an organizational intranet, the Internet, or networks equivalent thereto.

What is claimed is:

1. A system for guided surgery comprising:
a sensor for coupling to a first bone to receive positional signals;
a beacon for coupling to an object to provide the positional signals to the sensor, the object comprising one of a second bone and a surgical tool;
a patient-specific jig (PSJ) for guiding a relative position of the sensor and the first bone during coupling to position the sensor in a predetermined pose in an anatomical coordinate frame, the PSJ comprising a mirroring surface preoperatively formed to mirror an anatomical surface of the first bone, the mirroring surface configured to mate with the anatomical surface of the first bone; and
wherein the sensor is in communication with an intra-operative computing unit configured to calculate poses of the beacon with respect to the anatomical coordinate frame utilizing pre-operative data representing the PSJ and display positional information for the object in real time;
wherein one of the beacon and PSJ comprise a code optically encoding the pre-operative data representing the PSJ; and
wherein the intra-operative computing unit receives the code optically read from one of the beacon and PSJ to determine the pre-operative data representing the PSJ.

2. The system of claim 1 wherein the PSJ is configured to guide an insertion of at least two bone pins into the first bone and the sensor is configured to be rigidly attached to the at least two bone pins.

3. A system for guided surgery comprising:
a sensor for coupling to a first bone to receive positional signals;
a patient specific jig (PSJ) comprising a mirroring surface preoperatively formed to mirror an anatomical surface of the first bone, the mirroring surface configured to mate with the anatomical surface of the first bone and mount a beacon via the PSJ to the first bone;
a first beacon to provide the positional signals to the sensor, the first beacon for mounting to the first bone by the PSJ;
a second beacon to provide the positional signals to the sensor, the second beacon for coupling to an object comprising one of a second bone and a surgical tool;
wherein the sensor is in communication with an intra-operative computing unit configured to:
measure a pose of the first beacon when coupled to the bone via the PSJ to establish a positional relationship between the sensor and the PSJ;
calculate poses of the second beacon with respect to an anatomical coordinate frame utilizing pre-operative data representing the PSJ and the positional relationship between the sensor and the PSJ; and
display positional information for the object in real time.

4. The system of claim 3 wherein the first beacon and PSJ are integrally formed.

5. The system of claim 3 wherein the first beacon and second beacon are a single beacon, the first beacon being removable from the PSJ for coupling to the object.

6. The system of claim 3 wherein the surgery is a Total Hip Arthroplasty.

7. The system of claim 3 wherein the PSJ is a patient-specific acetabular jig.

8. The system of claim 3 wherein the object is the second bone and wherein the system further comprises a second PSJ for coupling a beacon to the second bone.

9. The system of claim 3 wherein the pre-operative data is represented by a code on one of the PSJ and the first beacon and wherein the sensor is configured to optically read the code and communicate the code to the computing unit for use to determine the pre-operative data.

10. The system of claim 3 wherein the sensor is an optical sensor and the first beacon and second beacon are optically trackable, providing respective positional signals via light.

11. A computer implemented method for tracking intra-operatively an object using a sensor to receive positional signals from a beacon, the sensor coupled to a first bone in a predetermined pose in an anatomical coordinate frame via a patient-specific jig (PSJ), the beacon coupled to the object, which object comprises one of a second bone and a surgical tool, the method comprising:
receiving a code optically read from one of the beacon and the PSJ, the code encoding pre-operative data representing the PSJ;
determining the pre-operative data using the code;
receiving positional information from the sensor at an intra-operative computing unit in communication with the sensor;
calculating poses of the beacon with respect to the anatomical coordinate frame utilizing the pre-operative data representing the PSJ; and
displaying positional information for the object in real time;
wherein, the PSJ comprises a mirroring surface preoperatively formed to mirror an anatomical surface of the first bone, the mirroring surface configured to mate with the anatomical surface of the first bone.

12. The method of claim 11 wherein the first bone is an acetabulum and the PSJ is pre-operatively formed to mate with the acetabulum, wherein the object is a femur and a second PSJ couples the beacon to the femur and wherein the calculating further utilizes pre-operative data representing the second PSJ.

13. A computer implemented method for tracking intra-operatively an object using a sensor to receive positional signals from a first beacon and a second beacon, the sensor coupled to a first bone, the first beacon coupled to the first bone via a patient specific jig (PSJ) comprising a mirroring surface preoperatively formed to mirror an anatomical surface of the first bone, the mirroring surface configured to mate with the anatomical surface of the first bone, the second beacon coupled to the object, which object comprises one of a second bone and a surgical tool, the method comprising:
receiving positional information from the sensor at an intra-operative computing unit in communication with the sensor;
measuring a pose of the first beacon when coupled to the first bone via the PSJ to establish a positional relationship between the sensor and the PSJ;
calculating poses of the second beacon with respect to an anatomical coordinate frame utilizing pre-operative data representing the PSJ and the positional relationship between the sensor and the PSJ; and
displaying positional information for the object in real time.

14. The method of claim 13 wherein the first beacon and second beacon are a single beacon, the first beacon being removable from the PSJ for coupling to the object.

15. The method of claim 13 wherein the method is performed during a Total Hip Arthroplasty.

16. The method of claim 13 wherein the first bone is an acetabulum and the PSJ is pre-operatively formed to mate with the acetabulum, wherein the object is a femur and wherein a second PSJ couples the second beacon to the femur and wherein the calculating further utilizes pre-operative data representing the second PSJ.

17. The method of claim 13 wherein the PSJ is pre-operatively formed based on an output of pre-operative planning software.

18. The method of claim 13 wherein initial positional data is measured using the pre-operative planning software and the method comprises comparing the poses calculated with the initial positional data and presenting results of the comparing.

19. The method of claim 18 wherein the initial positional data includes one or more of: leg length, offset and hip center of rotation.

20. The method of claim 13 comprising: receiving a code optically read from one of the first beacon and the PSJ, the code encoding pre-operative data representing the PSJ; and determining the pre-operative data using the code.

21. The method of claim 13 wherein the sensor is an optical sensor and the first beacon and second beacon are optically trackable, providing respective positional signals via light.

* * * * *